United States Patent [19]

Yeh

[11] Patent Number: 5,665,863

[45] Date of Patent: Sep. 9, 1997

[54] POLYPEPTIDES HAVING GRANULOCYTE COLONY STIMULATING ACTIVITY, THEIR PREPARATION AND PHARMACEUTICAL COMPOSITIONS CONTAINING THEM

[75] Inventor: Patrice Yeh, Paris, France

[73] Assignee: Rhone-Poulenc Rorer S.A., Antony, France

[21] Appl. No.: 256,938

[22] PCT Filed: Jan. 29, 1993

[86] PCT No.: PCT/FR93/00086

§ 371 Date: Jul. 27, 1994

§ 102(e) Date: Jul. 27, 1994

[87] PCT Pub. No.: WO93/15211

PCT Pub. Date: Aug. 5, 1993

[30] Foreign Application Priority Data

Jan. 31, 1992 [FR] France ................................. 92 01065

[51] Int. Cl.$^6$ ............................ C12N 15/27; C07K 14/53
[52] U.S. Cl. ................... 530/351; 424/85.1; 530/363; 435/69.5; 435/252.3; 435/320.1; 435/254.21; 435/254.2; 435/325; 435/360; 435/365.1
[58] Field of Search ................... 424/85.1, 85.2; 530/351, 363; 514/2; 435/69.5, 69.52, 240.1, 240.2, 252.3, 320.1

[56] References Cited

FOREIGN PATENT DOCUMENTS

| | | |
|---|---|---|
| 361 991 | 4/1990 | European Pat. Off. . |
| 364 980 | 4/1990 | European Pat. Off. . |
| 395 918 | 11/1990 | European Pat. Off. . |
| 401 384 | 12/1990 | European Pat. Off. . |
| 3723781 | 1/1988 | Germany . |
| WO90/13653 | 11/1990 | WIPO . |
| WO9102754 | 3/1991 | WIPO . |

OTHER PUBLICATIONS

Obayashi et al. (1991), Proc. of the Soc. of Exptal. Biol & Med., vol. 196, No. 2, pp. 164–169.

Williams et al. (1991) Int. J. of Cell Cloning vol. 9, pp. 542–547.

Williams et al (1990) Exp. Hematol. (N.Y.) vol. 18. (6), p. 615.

*Primary Examiner*—John Ulm
*Assistant Examiner*—Prema Mertz

[57] ABSTRACT

New polypeptides having granulocyte colony stimulating activity, preparation thereof and pharmaceutical compositions containing said polypeptides.

13 Claims, 13 Drawing Sheets

FIG. 1A

SEQ.ID NO: 1

| | |
|---|---|
| SEQUENCE TYPE: | Nucleotide and its corresponding protein |
| LENGTH: | 2382 nucleotides |
| STRANDEDNESS: | 1 |
| TOPOLOGY: | Linear |
| MOLECULE TYPE: | HindIII restriction fragment of the expression plasmid pYG1259 (chimera G.CSF-HSA) |
| ORIGINAL SOURCE: | in vitro genetic recombinations |

```
AAGCT TTACAACAAA TATAAAAACA ATG AAG TGG GTA ACC TTT ATT TCC CTT TTT CTC TTT       -12
                              Met Lys Trp Val Thr Phe Ile Ser Leu Phe Leu Phe

AGC TCG GCT TAT TCC AGG GGT GTG TTT CGT CGA GAT GCA CAC AAG AGT GAG GTT GCT CAT     9
Ser Ser Ala Tyr Ser Arg Gly Val Phe Arg Arg Asp Ala His Lys Ser Glu Val Ala His

CGG TTT AAA GAT TTG GGA GAA GAA AAT TTC AAA GCC TTG GTG TTG ATT GCC TTT GCT CAG    29
Arg Phe Lys Asp Leu Gly Glu Glu Asn Phe Lys Ala Leu Val Leu Ile Ala Phe Ala Gln

TAT CTT CAG CAG TGT CCA TTT GAA GAT CAT GTA AAA TTA GTG AAT GAA GTA ACT GAA TTT    49
Tyr Leu Gln Gln Cys Pro Phe Glu Asp His Val Lys Leu Val Asn Glu Val Thr Glu Phe

GCA AAA ACA TGT GTT GCT GAT GAG TCA GCT GAA AAT TGT GAC AAA TCA TCA CTT CAT CTT    69
Ala Lys Thr Cys Val Ala Asp Glu Ser Ala Glu Asn Cys Asp Lys Ser Leu His Thr Leu

TTT GGA GAC AAA TTA TGC ACA GTT GCA ACT CTT CGT CTT GAA ACC TAT GGT GAA ATG GCT GAC   89
Phe Gly Asp Lys Leu Cys Thr Val Ala Thr Leu Arg Glu Thr Tyr Gly Glu Met Ala Asp

TGC TGT GCA AAA CAA GAA CCT GAG AGA AAT GAA TGC TTC TTG CAA CAC AAA GAT GAC AAC   109
Cys Cys Ala Lys Gln Glu Pro Glu Arg Asn Glu Cys Phe Leu Gln His Lys Asp Asp Asn

CCA AAC CTC CCC CGA TTG GTG AGA CCA GTT GAT GTG ATG TGC ACT GCT TTT CAT GAC       129
Pro Asn Leu Pro Arg Leu Val Arg Pro Val Asp Val Met Cys Thr Ala Phe His Asp
```

FIG. 1B

```
AAT GAG ACA TTT TTG AAA AAA TAC TTA TAT GAA ATT GCC AGA CAT CCT TAC TTT       149
Asn Glu Thr Phe Leu Lys Lys Tyr Leu Tyr Glu Ile Ala Arg His Pro Tyr Phe

TAT GCC CCG GAA CTC TTT CTT TTT GCT TTC TTT GCT GCT AGG TAT AAA GCT TTT ACA GAA TGT TGC   169
Tyr Ala Pro Glu Leu Phe Leu Phe Ala Phe Phe Ala Ala Arg Tyr Lys Ala Phe Thr Glu Cys Cys

CAA GCT GCT GAT AAA GCT GCC AGT GCC TGC TTG CCA AAG CTC GAT GAA CTT CGG GAT GAA GGG       189
Gln Ala Ala Asp Lys Ala Ala Ser Ala Cys Leu Pro Lys Leu Asp Glu Leu Arg Asp Glu Gly

AAG GCT TCG TCT GCC AAA AGA CTC AAG TGT GCC CTC CAA AAA TTT GGA GAA AGA                   209
Lys Ala Ser Ser Ala Lys Arg Leu Lys Cys Ala Leu Gln Lys Phe Gly Glu Arg Arg

GCT TTC AAA GCA GTA GCT CGC CAG CTG CTG AGA AGA TTT CCC AAA GCT GAG TTT GCA               229
Ala Phe Lys Ala Val Ala Arg Gln Leu Leu Arg Arg Phe Pro Lys Ala Glu Phe Ala

GAA GTT TCC AAG TTA GTG ACA GAT CTT ACC AAA GTC CAC ACG GAA TGC TGC CAT GGA GAT            249
Glu Val Ser Lys Leu Val Thr Asp Leu Thr Lys Val His Thr Glu Cys Cys His Gly Asp

CTG CTT GAA TGT GCT GAT GAC AGG GCG GAC CTT GCC AAG TAT ATC TGT GAA AAT CAA GAT            269
Leu Leu Glu Cys Ala Asp Asp Arg Ala Asp Leu Ala Lys Tyr Ile Cys Glu Asn Gln Asp

TCG ATC TCC AGT AAA CTG AAA GAA TGC TGC GAA AAA CCT CTG CTG GAA AAA TCC CAC TGC            289
Ser Ile Ser Ser Lys Leu Lys Glu Cys Cys Glu Lys Pro Leu Leu Glu Lys Ser His Cys

ATT GCC GAA GTG GAA AAT GAT GAG ATG CCT GCT GAC TTG CCT TCA TTA GCT GCT GAT TTT            309
Ile Ala Glu Val Glu Asn Asp Glu Met Pro Ala Asp Leu Pro Ser Leu Ala Ala Asp Phe

GTT GAA AGT AAG GAT GTT TGC AAA AAC TAT GCT GAG GCA AAG GAT GTC TTC CTG GGC ATG            329
Val Glu Ser Lys Asp Val Cys Lys Asn Tyr Ala Glu Ala Lys Asp Val Phe Leu Gly Met

TTT TTG TAT GAA TAT GCA AGA AGG CAT CCT GAT TAC TCT GTC GTA CTG CTG CTG AGA CTT            349
Phe Leu Tyr Glu Tyr Ala Arg Arg His Pro Asp Tyr Ser Val Val Leu Leu Leu Arg Leu
```

FIG. 1C

```
GCC AAG ACA TAT GAA ACC ACT CTA GAG AAG TGC TGT GCC GCT GCA GAT CCT CAT GAA TGC    369
Ala Lys Thr Tyr Glu Thr Thr Leu Glu Lys Cys Cys Ala Ala Ala Asp Pro His Glu Cys

TAT GCC AAA GTG TTC GAT GAA ACC ACT CTT GTG GAA GAG CCT CTT AAA CCT CTT GTG GAA GAG CCT CTT AAA CCT CAG AAT TTA ATC AAA    389
Tyr Ala Lys Val Phe Asp Glu Phe Lys Pro Leu Val Glu Glu Pro Gln Asn Leu Ile Lys

CAA AAT TGT GAG CTT TTT GAG CAG CTT GGA GAG TAC TTG GAG TAC AAA TTC CAG AAT GCG CTA TTA GTT    409
Gln Asn Cys Glu Leu Phe Glu Gln Leu Gly Glu Tyr Lys Phe Gln Asn Ala Leu Leu Val

CGT TAC ACC AAG AAA GTA CCC CAA GTG TCA ACT CTT GTA GAG GTC TCA AGA AAC    429
Arg Tyr Thr Lys Lys Val Pro Gln Val Ser Thr Pro Thr Leu Val Glu Val Ser Arg Asn

CTA GGA AAA GTG GGC AGC AAA TGT TGT AAA CAT CCT GAA GCA GCA ATG AGA ATG CCC TGT GCA    449
Leu Gly Lys Val Gly Ser Lys Cys Cys Lys His Pro Glu Ala Lys Arg Met Pro Cys Ala

GAA GAC TAT CTA TCC GTG GTC TTA AAC CAG TTA TGT GTG TTG CAT GAG AAA ACG CCA GTA    469
Glu Asp Tyr Leu Ser Val Val Leu Asn Gln Leu Cys Val Leu His Glu Lys Thr Pro Val

AGT GAC AGA GTC ACC AAA TGC TGC ACA GAA TCC TTG GTG AAC AGG CGA CCA TGC TTT TCA    489
Ser Asp Arg Val Thr Lys Cys Cys Thr Glu Ser Leu Val Asn Arg Arg Pro Cys Phe Ser

GCT CTG GAA GTC GAT GAA ACA TAC GTT CCC AAA GAG TTT AAT GCT GAA ACA TTC ACC TTC    509
Ala Leu Glu Val Asp Glu Thr Tyr Val Pro Lys Glu Phe Asn Ala Glu Thr Phe Thr Phe

CAT GCA GAT ATA TGC ACA CTT TCT GAG AAG GAG AGA CAA ATC AAG AAA CAA ACT GCA CTT    529
His Ala Asp Ile Cys Thr Leu Ser Glu Lys Glu Arg Gln Ile Lys Lys Gln Thr Ala Leu

GTT GAG CTT GTG AAA CAC AAG CCC AAG GCA ACA AAA GAG CAA CTG AAA GCT GTT ATG GAT    549
Val Glu Leu Val Lys His Lys Pro Lys Ala Thr Lys Glu Gln Leu Lys Ala Val Met Asp

GAT TTC GCA GCT TTT GTA GAG AAG TGC TGC AAG GCT GAC GAT AAG GAG ACC TGC TTT GCC    569
Asp Phe Ala Ala Phe Val Glu Lys Cys Cys Lys Ala Asp Asp Lys Glu Thr Cys Phe Ala
```

```
GAG GAG GGT AAA AAA CTT GTT GCT GCA AGT CAA GCT GCC TTA GGC TTA ACC CCC CTG GGC   589
Glu Glu Gly Lys Lys Leu Val Ala Ala Ser Gln Ala Ala Leu Gly Leu Thr Pro Leu Gly

CCT GCC AGC TCC CTG CCC CAG AGC TTC CTG CTC AAG TGC TTA GAG CAA GTG AGG AAG ATC   609
Pro Ala Ser Ser Leu Pro Gln Ser Phe Leu Leu Lys Cys Leu Glu Gln Val Arg Lys Ile

CAG GGC GAT GCC GCA GCG CTC CAG GAG AAG CTG TGT GCC ACC TAC AAG CTG TGC CAC CCC   629
Gln Gly Asp Ala Ala Ala Leu Gln Glu Lys Leu Cys Ala Thr Tyr Lys Leu Cys His Pro

GAG GAG CTG GTG CTG GGA CAC TCT CTG GGC ATC CCC TGG GCT CCC CTG AGC TCC TGC       649
Glu Glu Leu Val Leu Gly His Ser Leu Gly Ile Pro Trp Ala Pro Leu Ser Ser Cys

CCC AGC CAG CTG GCA CAG CTG CTG GCA GGG TGC TTG AGC CAA CTC CAT AGC GGC CTT TTC CTC   669
Pro Ser Gln Leu Ala Gln Leu Leu Ala Gly Cys Leu Ser Gln Leu His Ser Gly Leu Phe Leu

TAC CAG GGG CTC GGG CTC CAG GCC CTG GAA GGG ATA CTG GAG TTG GGT CCC ACC TTG GAC   689
Tyr Gln Gly Leu Gly Leu Gln Ala Leu Glu Gly Ile Leu Glu Leu Gly Pro Thr Leu Asp

ACA CTG CAG CTG GAC GTC GCC GAC TTT GCC ACC ATC TGG CAG CAG ATG GAA GAA CTG       709
Thr Leu Gln Leu Asp Val Ala Asp Phe Ala Thr Ile Trp Gln Gln Met Glu Glu Leu

GGA ATG GCC CCT GCC CTG CAG CCC ACC CAG GGT GCC ATG CCG GCC TTC GCC TCT GCT TTC   729
Gly Met Ala Pro Ala Leu Gln Pro Thr Gln Gly Ala Met Pro Ala Phe Ala Ser Ala Phe

CAG CGC CGG GCA GGA GGG GTC CTG GTT GCG AGC CAT CTG CAG AGC TTC CTG GAG GTG TCG   749
Gln Arg Arg Ala Gly Gly Val Leu Val Ala Ser His Leu Gln Ser Phe Leu Glu Val Ser

TAC CGC GTT CTA CGC CAC CTT GCG CAG CCC TGA AGCTT                                 759
Tyr Arg Val Leu Arg His Leu Ala Gln Pro ***
```

```
SEQ.ID NO: 2

SEQUENCE TYPE:      Nucleotide and its corresponding protein
LENGTH:             2455 nucleotides
STRANDEDNESS:       1
TOPOLOGY:           Linear
MOLECULE TYPE:      HindIII restriction fragment of the expression
                    plasmid pYG1301 (chimera G.CSF-Gly₄-HSA
                    positioned immediately downstream of the HSA
                    prepro region)
ORIGINAL SOURCE:    in vitro genetic recombinations AAGCT TTACAACAAA TATAAAAACA ATG AAG TGG GTA ACC TTT ATT TCC CTT TTT CTC TTT                        -12
                            Met Lys Trp Val Thr Phe Ile Ser Leu Phe Leu Phe AGC TCG GCT TAT TCC AGG GGT GTG TTT CGT CGA ACC CCC CTG GGC CCT GCC AGC TCC CTG                      9
Ser Ser Ala Tyr Ser Arg Gly Val Phe Arg Arg Thr Pro Leu Gly Pro Ala Ser Ser Leu
                                                         ApaI
                                                           I---->G-CSF
CCC CAG AGC TTC CTG CTC AAG TGC TTA GAG CAA GTG CGA AAG ATC CAG GGC GAT GGC GCA                     29
Pro Gln Ser Phe Leu Leu Lys Cys Leu Glu Gln Val Arg Lys Ile Gln Gly Asp Gly Ala GCG CTC CAG GAG AAG CTG TGT GCC ACC TAC AAG CTG TGC CAC CCC GAG CTG GTG GTG CTG                     49
Ala Leu Gln Glu Lys Leu Cys Ala Thr Tyr Lys Leu Cys His Pro Glu Leu Val Val Leu
                                                       SstI
CTC GGA CAC TCT CTG GGC ATC CCC TGG GCT CCC CTG AGC TCC TGC CCC AGC CAG GCC CTG                     69
Leu Gly His Ser Leu Gly Ile Pro Trp Ala Pro Leu Ser Ser Cys Pro Ser Gln Ala Leu CAG CTG GCA GGC TGC TTG AGC CAA CTC CAT AGC GGC CTT TTC CTC TAC CAG GGG CTC CTG                     89
Gln Leu Ala Gly Cys Leu Ser Gln Leu His Ser Gly Leu Phe Leu Tyr Gln Gly Leu Leu CAG GCC CTG GAA GGG ATA TCC CCG GAG TTG GGT CCC ACC TTG GAC ACA CTG CAG CTG GAC                    109
Gln Ala Leu Glu Gly Ile Ser Pro Glu Leu Gly Pro Thr Leu Asp Thr Leu Gln Leu Asp
```

FIG. 5B

| GTC | GCC | GAC | TTT | GCC | ACC | ACC | ATC | TGG | CAG | CAG | ATG | GAA | GAA | CTG | GGA | ATG | GCC | CCT | GCC | 129 |
| Val | Ala | Asp | Phe | Ala | Thr | Thr | Ile | Trp | Gln | Gln | Met | Glu | Glu | Leu | Gly | Met | Ala | Pro | Ala | |

| CTG | CAG | CCC | ACC | CAG | GGT | GCC | ATG | CCG | GCC | TTC | GCC | TCT | GCT | TTC | CAG | CGC | CGG | GCA | GGA | 149 |
| Leu | Gln | Pro | Thr | Gln | Gly | Ala | Met | Pro | Ala | Phe | Ala | Ser | Ala | Phe | Gln | Arg | Arg | Ala | Gly | |

| GGG | GTC | CTG | GTT | GCT | AGC | CAT | CTG | CAG | AGC | TTC | CTG | GAG | GTG | TCG | TAC | CGC | GTT | CTA | CGC | 169 |
| Gly | Val | Leu | Val | Ala | Ser | His | Leu | Gln | Ser | Phe | Leu | Glu | Val | Ser | Tyr | Arg | Val | Leu | Arg | |

| CAC | CTT | GCG | CAG | CCC | GGT | GGA | GGC | GGT | GAT | GCA | CAC | AAG | AGT | GAG | GTT | GCT | CAT | CGG | TTT | 189 |
| His | Leu | Ala | Gln | Pro | Gly | Gly | Gly | Gly | Asp | Ala | His | Lys | Ser | Glu | Val | Ala | His | Arg | Phe | |

G-CSF <---I linker I---> HSA

| AAA | GAT | TTG | GGA | GAA | GAA | AAT | TTC | AAA | GCC | TTG | GTG | TTG | ATT | GCC | TTT | GCT | CAG | TAT | CTT | 209 |
| Lys | Asp | Leu | Gly | Glu | Glu | Asn | Phe | Lys | Ala | Leu | Val | Leu | Ile | Ala | Phe | Ala | Gln | Tyr | Leu | |

| CAG | CAG | TGT | CCA | TTT | GAA | GAT | CAT | GTA | AAA | TTA | GTG | AAT | GAA | GTA | ACT | GAA | TTT | GCA | AAA | 229 |
| Gln | Gln | Cys | Pro | Phe | Glu | Asp | His | Val | Lys | Leu | Val | Asn | Glu | Val | Thr | Glu | Phe | Ala | Lys | |

| ACA | TGT | GTT | GCT | GAT | GAG | TCA | GCT | GAA | AAT | TGT | GAC | AAA | TCA | CTT | CAT | ACC | CTT | TTT | GGA | 249 |
| Thr | Cys | Val | Ala | Asp | Glu | Ser | Ala | Glu | Asn | Cys | Asp | Lys | Ser | Leu | His | Thr | Leu | Phe | Gly | |

| GAC | AAA | TTA | TGC | ACA | GTT | GCA | ACT | CTT | CGT | GAA | ACC | TAT | GGT | GAA | ATG | GCT | GAC | TGC | TGT | 269 |
| Asp | Lys | Leu | Cys | Thr | Val | Ala | Thr | Leu | Arg | Glu | Thr | Tyr | Gly | Glu | Met | Ala | Asp | Cys | Cys | |

| GCA | AAA | CAA | GAA | CCT | GAG | AGA | AAT | GAA | TGC | TTC | TTG | CAA | CAC | AAG | GAT | GAC | AAC | CCA | AAC | 289 |
| Ala | Lys | Gln | Glu | Pro | Glu | Arg | Asn | Glu | Cys | Phe | Leu | Gln | His | Lys | Asp | Asp | Asn | Pro | Asn | |

| CTC | CCC | CGA | TTG | GTG | AGA | CCA | GAG | GTT | GAT | GTG | ATG | TGC | ACT | GCT | TTT | CAT | GAC | AAT | GAA | 309 |
| Leu | Pro | Arg | Leu | Val | Arg | Pro | Glu | Val | Asp | Val | Met | Cys | Thr | Ala | Phe | His | Asp | Asn | Glu | |

| GAG | ACA | TTT | TTG | AAA | TAC | TTA | TAT | GAA | ATT | GCC | AGA | AGA | CAT | CCT | TAC | TTT | TAT | GCC | 329 |
| Glu | Thr | Phe | Leu | Lys | Tyr | Leu | Tyr | Glu | Ile | Ala | Arg | Arg | His | Pro | Tyr | Phe | Tyr | Ala | |

```
CCG GAA CTC CTT TTT GCT AAA AGG TAT AAA GCT GCT TTT ACA GAA TGT CAA GCT      349
Pro Glu Leu Leu Phe Ala Lys Arg Tyr Lys Ala Ala Phe Thr Glu Cys Gln Ala

GCT GAT AAA GCT GCC TGC CTG TTG CCA AAG CTC GAT GAA CTT CGG GAT GAA GGG AAG GCT  369
Ala Asp Lys Ala Ala Cys Leu Leu Pro Lys Leu Asp Glu Leu Arg Asp Glu Gly Lys Ala

TCG TCT GCC AAA CAG CTC AGA AAG TGC CAA AGT GCC CTC CAA TTT GGA GAA AGA GCT TTC  389
Ser Ser Ala Lys Gln Leu Arg Lys Cys Ala Ser Leu Gln Lys Phe Gly Glu Arg Ala Phe

AAA GCA TGG GCA GTA GCT CGC CTG AGC CAG AGA TTT CCC AAA GCT GAG TTT GCA GAA GTT  409
Lys Ala Trp Ala Val Ala Arg Leu Ser Gln Arg Phe Pro Lys Ala Glu Phe Ala Glu Val

TCC AAG TTA GTG ACA GAT CTT ACC AAA GTC CAC ACG GAA TGC TGC CAT GGA GAT CTG CTT  429
Ser Lys Leu Val Thr Asp Leu Thr Lys Val His Thr Glu Cys Cys His Gly Asp Leu Leu

GAA TGT GCT GAT GAC AGG GCG GAC CTT GCC AAG TAT ATC TGT GAA AAT CAA GAT TCG ATC  449
Glu Cys Ala Asp Asp Arg Ala Asp Leu Ala Lys Tyr Ile Cys Glu Asn Gln Asp Ser Ile

TCC AGT AAA CTG AAG GAA TGT TGT GAA AAA CCT CTG CTT GAA TTA CCT TCA CAC TGC ATT GCC  469
Ser Ser Lys Leu Lys Glu Cys Cys Glu Lys Pro Leu Leu Glu Lys Ser His Cys Ile Ala

GAA GTG GAA AAT GAT GAG ATG CCT GCT GAC TTG CCT TCA GCT GAT GTC TTC CTG GGC ATG TTT TTG GAA  489
Glu Val Glu Asn Asp Glu Met Pro Ala Asp Leu Pro Ser Leu Ala Asp Val Phe Leu Gly Met Phe Leu Glu

AGT AAG GAT GTT TGC AAA AAC TAT GCA CAT CCT GAT TAC TCT GTA GTG CTG CTG AGA CTT GTT GAA  509
Ser Lys Asp Val Cys Lys Asn Tyr Ala His Pro Asp Tyr Ser Val Val Leu Leu Arg Leu Val Glu

TAT GAA TAT GCA AGA AGG CAT CCT GAT TAT TCT GTA GTG CTG CTG AGA CTT GCC AAG  529
Tyr Glu Tyr Ala Arg Arg His Pro Asp Tyr Ser Val Val Leu Leu Arg Leu Ala Lys

ACA TAT GAA ACC ACT CTA GAG AAG TGC TGT GCC GCT GCA GAT CCT CAT GAA TGC TAT GCC  549
Thr Tyr Glu Thr Thr Leu Glu Lys Cys Cys Ala Ala Ala Asp Pro His Glu Cys Tyr Ala
```

FIG. 5C

```
AAA GTG TTC GAT GAA TTT AAA CCT CTT GTG GAA GAG CCT CAG AAT TTA ATC AAA CAA AAT   569
Lys Val Phe Asp Glu Phe Lys Pro Leu Val Glu Glu Pro Gln Asn Leu Ile Lys Gln Asn

TGT GAG CTT TTT GAG CAG CTT GGA GAG TAC AAA TTC CAG AAT GCG CTA TTA GTT CGT TAC   589
Cys Glu Leu Phe Glu Gln Leu Gly Glu Tyr Lys Phe Gln Asn Ala Leu Leu Val Arg Tyr

ACC AAG AAA GTA CCC CAA GTG TCA ACT CCA ACT CTT GTA GAG GTC TCA AGA AAC CTA GGA   609
Thr Lys Lys Val Pro Gln Val Ser Thr Pro Thr Leu Val Glu Val Ser Arg Asn Leu Gly

AAA GTG GGC AGC AAA TGT TGT AAA CAT CCT GAA GCA AAA AGA ATG CCC TGT GCA GAA GAC   629
Lys Val Gly Ser Lys Cys Cys Lys His Pro Glu Ala Lys Arg Met Pro Cys Ala Glu Asp

TAT CTA TCC GTG GTC CTG AAC CAG TTA TGT GTG TTG CAT GAG AAA ACG CCA GTA AGT GAC   649
Tyr Leu Ser Val Val Leu Asn Gln Leu Cys Val Leu His Glu Lys Thr Pro Val Ser Asp

AGA GTC ACC AAA TGC TGC ACA GAA TCC TTG GTG AAC AGG CGA CCA TGC TTT TCA GCT CTG   669
Arg Val Thr Lys Cys Cys Thr Glu Ser Leu Val Asn Arg Arg Pro Cys Phe Ser Ala Leu

GAA GTC GAT GAA ACA TAC GTT CCC AAA GAG TTT AAT GCT GAA ACA TTC ACC TTC CAT GCA   689
Glu Val Asp Glu Thr Tyr Val Pro Lys Glu Phe Asn Ala Glu Thr Phe Thr Phe His Ala

GAT ATA TGC ACA CTT TCT GAG AAG GAG AGA CAA ATC AAG AAA CAA ACT GCA CTT GTT GAG   709
Asp Ile Cys Thr Leu Ser Glu Lys Glu Arg Gln Ile Lys Lys Gln Thr Ala Leu Val Glu

CTT GTG AAA CAC AAG CCC AAG GCA ACA AAA GAG CAA CTG AAA GCT GTT ATG GAT GAT TTC   729
Leu Val Lys His Lys Pro Lys Ala Thr Lys Glu Gln Leu Lys Ala Val Met Asp Asp Phe

GCA GCT TTT GTA GAG TGC TGC CAA GCT GAT GAT AAG GAG ACC TGC TTT GCC GAG GAG       749
Ala Ala Phe Val Glu Cys Cys Gln Ala Asp Asp Lys Glu Thr Cys Phe Ala Glu Glu

GGT AAA AAA CTT GTT GCT GCA AGT CAA GCT GCC TTA TAA CATCACATT                     763
Gly Lys Lys Leu Val Ala Ala Ser Gln Ala Ala Leu Gly Leu ***
                                            MstII

AAAAGCATCT CAGCCTACCA TGAATAAG AGAAAGAAAA TGAAGATCAA AAGCTT
```

FIG. 5D

POLYPEPTIDES HAVING GRANULOCYTE COLONY STIMULATING ACTIVITY, THEIR PREPARATION AND PHARMACEUTICAL COMPOSITIONS CONTAINING THEM

The present invention relates to new polypeptides having human granulocyte colony stimulating activity, to their preparation and to pharmaceutical compositions containing them.

BACKGROUND OF THE INVENTION

The present invention relates especially to chimeric polypeptides composed of a biologically active portion consisting of all or part of G-CSF or of a variant of G-CSF, and an essentially proteinaceous stabilizing structure endowing it with new biological properties.

Human G-CSF is a secreted polypeptide of 174 amino acids having a molecular weight of approximately 18 kD. It was isolated initially from a cancer cell line (EP 169,566), and its gene has been cloned, sequenced and expressed in different cell hosts by genetic engineering techniques (EP 215,126, EP 220,520). An mRNA potentially coding for a form of G-CSF having 177 amino adds has, moreover, been detected [Nagata S. et al., EMBO J. 5 (1986) 575–581]. G-CSF possesses the capacity to stimulate the differentiation and proliferation of bone marrow stem cells to granulocytes. As such, it possesses the capacity to stimulate the body's protective capacities against infection by promoting the growth of polymorphonuclear neutrophils and their differentiation ending in maturity. It is thus capable of activating the body's prophylactic functions, and may be used in different pathological situations in which the number of neutrophils is abnormally low or in which the immune system needs to be strengthened. Such situations arise, for example, following cancer chemotherapy treatments, in transplantation, and especially bone marrow transplantation, or in leukopenic states.

One of the drawbacks of currently available G-CSF lies in the fact that it is rapidly degraded by the body once administered. This is all the more noticeable for the fact that G-CSF is generally used at low doses. Furthermore, the use of larger doses has not been able to permit therapeutic capacities of this molecule to be improved, and may induce adverse side effects. These phenomena of elimination and degradation in vivo hence constitute at present an obstacle to exploitation of the biological activity of the G-CSF as a pharmaceutical agent.

DESCRIPTION OF THE PREFERRED EMBODIMENTS

Figure 2A:
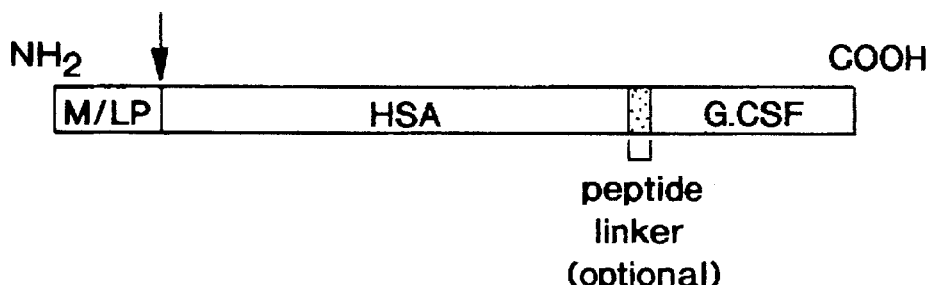

The present invention enables these drawbacks to be remedied. The present invention provides, in effect, new molecules enabling the biological properties of G-CSF to be optimally exploited from a therapeutic standpoint. The Applicant demonstrated, in effect, that optimal G-CSF activity was manifested when the G-CSF was present at a low dose and for a prolonged time. The Applicant has now produced molecules capable of maintaining G-CSF activity in the body for a sufficiently long time. Furthermore, the Applicant has shown that it is possible to express, in cell hosts at high levels, genetic fusion generating chimeras possessing new pharmacokinetic properties and the desirable biological properties of G-CSF. In particular, hybrid polypeptides of the invention retain their affinity for G-CSF receptors, and are sufficiently functional to lead to proliferation and to cell differentiation. The molecules of the invention possess, moreover, a distribution and pharmacokinetic properties which are especially advantageous in the body, and enable their biological activity to be developed therapeutically.

A subject of the present invention hence relates to recombinant polypeptides containing an active portion consisting of all or part of G-CSF, or of a variant of G-CSF, and an essentially proteinaceous stabilizing structure.

For the purposes of the present invention, the term variant of G-CSF denotes any molecule obtained by modification of the sequence lying between the residues Thr586 and Pro759 of the sequence presented in FIG. 1, retaining G-CSF activity, that is to say the capacity to stimulate the differentiation of target cells and the formation of granulocyte colonies. This sequence corresponds to that of mature G-CSF described by Nagata et al. [EMBO J. 5 (1986) 575–581 ]. Modification is understood to mean any mutation, substitution, deletion, addition or modification resulting from an action of a genetic and/or chemical nature. Such variants may be generated for different purposes, such as, in particular, that of increasing the affinity of the molecule for the G-CSF receptor(s), that of improving its levels of production, that of increasing its resistance to proteases, that of increasing its therapeutic efficacy or of reducing its side effects, or that of endowing it with new pharmacokinetic and/or biological properties.

Especially advantageous polypeptides of the invention are those in which the biologically active portion possesses:

(a) the peptide sequence lying between the residues Thr586 and Pro759 of the sequence presented in FIG. 1, or (b) a portion of the structure (a), or (c) a structure derived from the structures (a) or (b) by structural modifications (mutation, addition substitution and/or deletion of one or more residues), and having an identical or modified biological activity. This latter type of polypeptide comprises, for example, molecules in which some glycosylation sites have been modified or eliminated, as well as molecules in which one, several or even all the cysteine residues have been substituted. It also comprises molecules obtained from (a) or (b) by deletion of regions that display little or no participation in the activity or which participate in an undesirable activity, and molecules containing, relative to (a) or (b), additional residues such as, for example, an N-terminal methionine or a secretion signal.

More preferably, the chimeric polypeptides of the invention comprise an active portion of type (a).

The active portion of the molecules of the invention may be coupled to the proteinaceous stabilizing structure either directly or via a peptide linker. Furthermore, it can constitute the N-terminal end or the C-terminal end of the molecule. Preferably, in the molecules of the invention, the active portion constitutes the C-terminal portion of the chimera.

As stated above, the stabilizing structure of the polypeptides of the invention is essentially proteinaceous.

Preferably, this structure is a polypeptide possessing a long plasma half-life. As an example, it can be an albumin, an apolipoprotein, an immunoglobulin or alternatively a transferrin. Appropriate peptides can also be ones derived from such proteins by structural modifications, or artificially or semi-artificially synthesized peptides possessing a long plasma half-life. Moreover, the stabilizing structure used is, more preferably, a polypeptide which is weakly immunogenic or non-immunogenic for the organism in which the polypeptides of the invention are used.

In an especially advantageous embodiment of the invention, the stabilizing structure is an albumin or a variant of albumin, and for example human serum albumin (HSA). It is understood that variants of albumin denote any protein having a long plasma half-life obtained by modification (mutation, deletion and/or addition) by genetic engineering techniques of a gene coding for a given isomorph of human serum albumin, as well as any macromolecule having a long plasma half-life obtained by in vitro modification of the protein encoded by such genes. Since albumin is very polymorphic, many natural variants have already been identified, and more than 30 different genetic types have been listed [Weitkamp L. R. et al., Ann. Hum. Genet. 37 (1973) 219]. More preferably, the stabilizing structure is a mature albumin.

As examples, there may be mentioned polypeptides of the invention containing, in the N-terminal→C-terminal direction, (i) the mature HSA sequence coupled directly to the mature G-CSF sequence (see FIG. 1), or (ii) the mature G-CSF sequence coupled via a peptide linker to the mature HSA sequence.

Another subject of the invention relates to a method for preparing the chimeric molecules described above. More specifically, this method consists in causing a eukaryotic or prokaryotic cell host to express a nucleotide sequence coding for the desired polypeptide, and in then harvesting the polypeptide produced.

Among eukaryotic hosts which are usable in the context of the present invention, animal cells, yeast or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127, and the like, cells may be mentioned. Among fungi capable of being used in the present invention, Aspergillus ssp. or Trichoderma ssp. may be mentioned more especially. As prokaryotic hosts, it is preferable to use bacteria such as Escherichia coil, or ones belonging to the genera Corynebacterium, Bacillus or Streptomyces.

The nucleotide sequences which are usable in the context of the present invention may be prepared in different ways. Generally, they are obtained by assembling in a reading frame the sequences coding for each of the functional portions of the polypeptide. These may be isolated by the techniques of a person skilled in the art, and, for example, directly from the cellular messenger RNAs (mRNAs), or by recloning from a library of complementary DNA (cDNA) isolated from cells that make the product, or alternatively the nucleotide sequences in question may be completely synthetic ones. It is understood, furthermore, that the nucleotide sequences may also be modified subsequently, for example by genetic engineering techniques, to obtain derivatives or variants of the said sequences.

More preferably, in the method of the invention, the nucleotide sequence forms part of an expression cassette comprising a transcription initiation region (promoter region) permitting, in the host cells, expression of the nucleotide sequence placed under its control and coding for the polypeptides of the invention. This region can originate from promoter regions of genes which are strongly expressed in the host cell used, the expression being constitutive or regulable. As regards yeasts, the promoter can be that of the gene for phosphoglycerate kinase (PGK); for glyceraldehyde-3-phosphate dehydrogenase (GPD), for lactase (LAC4), for enolases (ENO), for alcohol dehydrogenases (ADH), and the like. As regards bacteria, the promoter can be that of the right or left genes of bacteriophage lambda ($P_L$, $P_R$), or alternatively those of the genes of the tryptophan ($P_{trp}$) or lactose ($P_{lac}$) operons. In addition, this control region may be modified, for example by in vitro mutagenesis, by the introduction of additional control elements or of synthetic sequences or by deletions or substitutions of the original control elements. The expression cassette can also comprise a transcription termination region which is functional in the host envisaged, positioned immediately downstream of the nucleotide sequence coding for a polypeptide of the invention.

In a preferred embodiment, the polypeptides of the invention result from the expression of a nucleotide sequence in a eukaryotic or prokaryotic host and the secretion of the expression product of the said sequence into the culture medium. It is, in effect, especially advantageous to be able to obtain molecules directly in the culture medium using recombinant methods. In this case, the nucleotide sequence coding for a polypeptide of the invention is preceded by a leader sequence (or signal sequence) directing the nascent polypeptide into the pathways of secretion of the host used. This leader sequence can be the natural signal sequence of G-CSF or of the stabilizing structure in the case where the latter is a naturally secreted protein, but it can also be any other functional leader sequence, or an artificial leader sequence. The choice of one or other of these sequences is, in particular, guided by the host used. Examples of functional signal sequences include those of the genes for the sex pheromones or for the killer toxins of yeasts.

In addition to the expression cassette, one or more markers enabling the recombinant host to be selected may be added, such as, for example, the URA3 gene of S. cerevisiae yeast, or genes conferring resistance to antibiotics such as geneticin (G418) or to any other toxic compound such as certain metal ions.

The assembly consisting of the expression cassette and the selectable marker may be introduced, either directly into the host cells in question, or inserted beforehand into a functional self-replicating vector. In the first case, sequences homologous With regions present in the genome of the host cells are preferably added to this assembly; the said sequences then being positioned on each side of the expression cassette and the selectable gene so as to increase the frequency of integration of the assembly in the host's genome by targeting integration of the sequences by homologous recombination. In the case where the expression cassette is inserted into a replicating system, a preferred replication system for yeasts of the genus Kluyveromyces is derived from plasmid pKD1 initially isolated from K. drosophilarum; a preferred replication system for yeasts of the genus Saccharomyces is derived from the 2µ plasmid of S. cerevisiae. Furthermore, this expression plasmid can contain all or part of the said replication systems, or can combine elements derived from plasmid pKD1 as well as from the 2µ plasmid.

In addition, the expression plasmids can be shuttle vectors between a bacterial host such as Escherichia coil and the chosen host cell. In this case, an origin of replication and a selectable marker that function in the bacterial host are required. It is also possible to position restriction sites surrounding the bacterial and unique sequences on the expression vector: this enables the sequences to be eliminated by cutting and religation in vitro of the truncated vector before transformation of the host cells, which can result in an increase in copy number and in an enhanced stability of the expression plasmids in the said hosts. For example, such restriction sites can correspond to sequences such as 5'-GGCCNNNNNGGCC-3' (SEQ ID NO: 5, SfiI) or 5'-GCGGCCGC-3' (NotI), inasmuch as these sites are extremely rare and generally absent from an expression vector.

After the construction of such expression vectors or cassette, these are introduced into the selected host cells according to standard techniques described in the literature. In this connection, any method enabling a foreign DNA to be introduced into a cell may be used. This can comprise, in particular, transformation, electroporation, conjugation or any other technique known to a person skilled in the art. As an example for yeast type hosts, the different Kluyveromyces strains used have been transformed by treating the whole cells in the presence of lithium acetate and polyethylene glycol, according to a technique described by Ito et al. [J. Bacteriol. 153 (1983) 163]. The transformation technique described by Durrens et al. [Curr. Genet. 18 (1990) 7] using ethylene glycol and dimethyl sulphoxide has also been used. It is also possible to transform yeasts by electroporation, according to the method described by Karube et al. [FEBS Letters 182 (1985) 90]. An alternative protocol is also described in detail in the examples which follow.

After selection of the transformed cells, the cells expressing the said polypeptides are inoculated and recovery of the said polypeptides may be carried out, either during cell growth for "continuous" methods, or at the end of growth for "batch" cultures. The polypeptides which form the subject of the present invention are then purified from the culture supernatant for the purpose of their molecular, pharmacokinetic and biological characterization.

A preferred expression system for the polypeptides of the invention consists in using yeasts of the genus Kluyveromyces as host cell, the yeasts being transformed with certain vectors derived from the extrachromosomal replicon pKD1 initially isolated in K. marxianus var. drosophilarum. These yeasts, and especially K. lactis and K. fragilis, are generally capable of stably replicating the said vectors, and possess, in addition, the advantage of being included in the list of GRAS (Generally Recognized As Safe) organisms. Favoured yeasts are preferably industrial strains of the genus Kluyveromyces which are capable of stably replicating the said plasmids derived from plasmid pKD1, and into which has been inserted a selectable marker as well as an expression cassette permitting the secretion of the polypeptides of the invention at high levels.

The present invention also relates to the nucleotide sequences coding for the chimeric polypeptides described above, as well as the recombinant eukaryotic or prokaryotic cells comprising such sequences.

The present invention also relates to the application of the polypeptides according to the present invention as a medicinal product. More especially, the subject of the invention is any pharmaceutical composition comprising one or more polypeptides as described above. More especially, these compositions may be used in all pathological situations in which the number and/or activity of granulocytes need to be stimulated. In particular, they may be used for the prevention or treatment of leukopenic states or of some leukaemias or, in the case of transplantation or of cancer treatment, for strengthening or restoring the immune system.

The present invention will be described more fully by means of the examples which follow, which are to be considered as illustrative and non-limiting.

LIST OF FIGURES

The representations of the plasmids shown in the following figures are not drawn to scale, and only the restriction sites which are important for an understanding of the clonings carried out have been shown.

FIG. 1: Nucleotide sequence (SEQ ID NO: 1 ) and deduced amino acid sequence (SEQ ID NO: 2) of the HindIII restriction fragment of plasmid pYG1259 (chimera prepro-HSA-G.CSF). The solid arrows indicate the end of the HSA "pre" and "pro" regions. The MstII, ApaI and SStI (SacI) restriction sites are underlined. The G-CSF peptide sequence is in italics (Thr586>Pro759; the numbering of the amino acids corresponds to the mature chimeric protein).

Figure 2B:
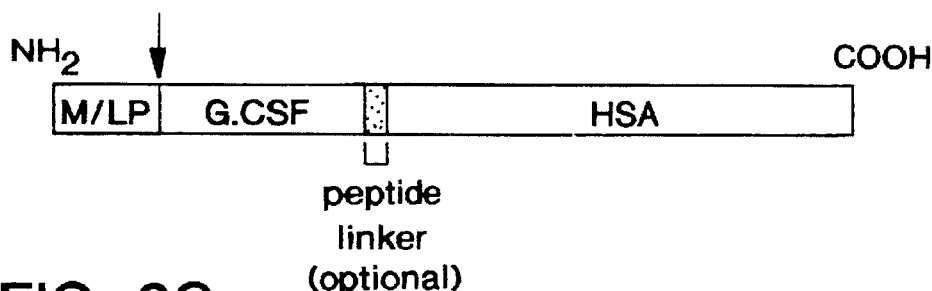
Figure 2C:
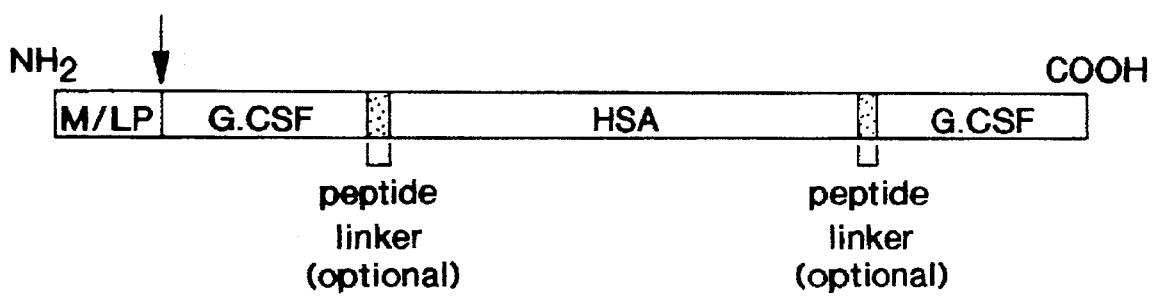

FIG. 2: Diagrammatic representation of chimeras of the HSA-G.CSF type (A) and of the G.CSF-HSA (B) or G.CSF-HSA-G.CSF (C) type. Abbreviations used: M/LP, translation initiation methionine, where appropriate followed by a secretion signal sequence; HSA, mature human serum albumin or one of its variants; G.CSF, peptide derived from G-CSF and having an identical or modified activity. The solid arrow indicates the N-terminal end of the mature protein.

Figure 3:
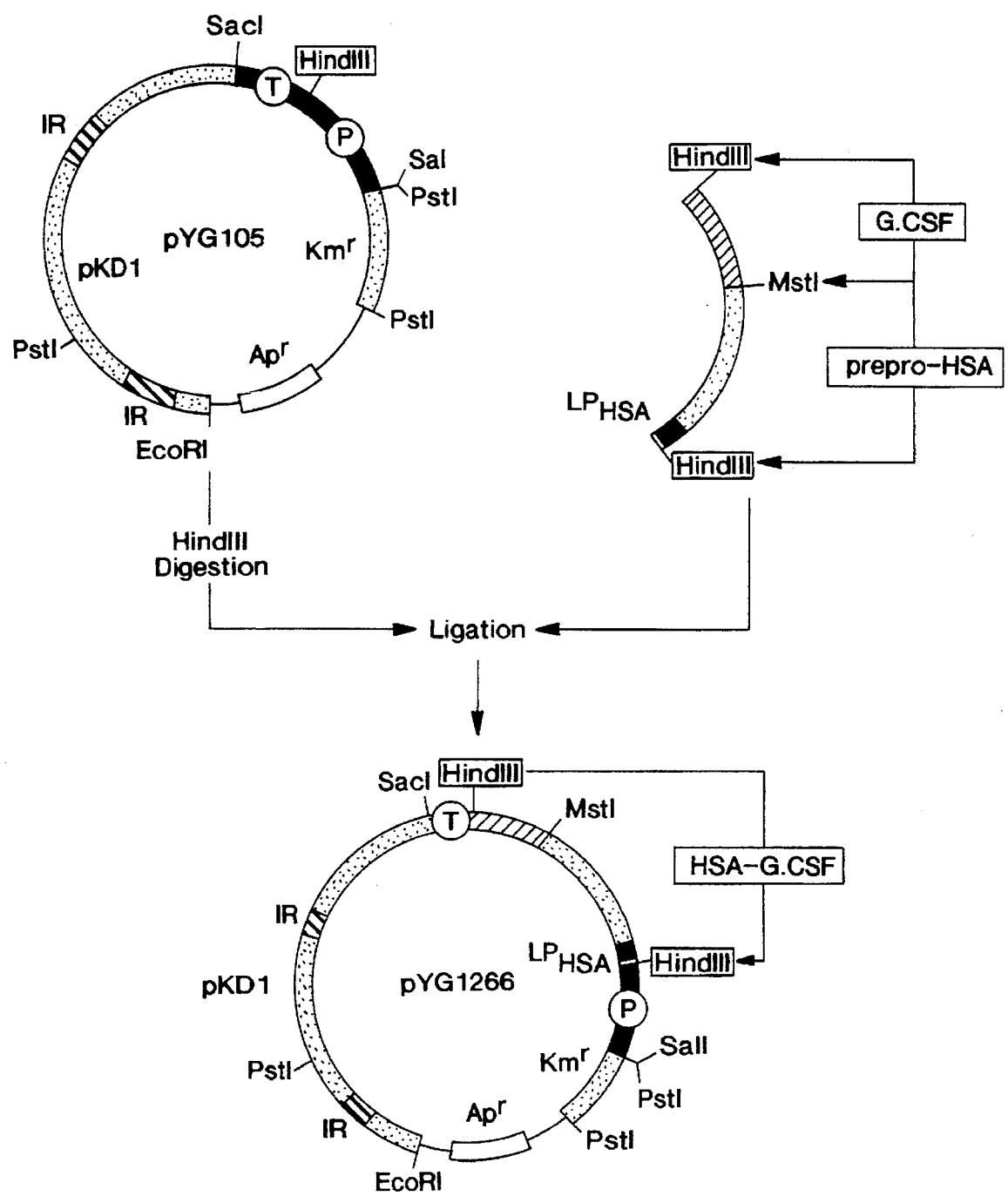

FIG. 3: Restriction map of plasmid pYG105, and strategy of construction of the plasmids for the expression of the chimeric proteins of the present invention. Abbreviations used: P, transcription promoter; T, transcription terminator; IR, inverted repeat sequences of plasmid pKD1; $LP_{HSA}$, HSA "prepro" region; $Ap^r$ and $Km^r$ denote, respectively, the genes for resistance to ampicillin (E. coli) at to G418 (yeasts).

Figures 4A, 4B, 4C:
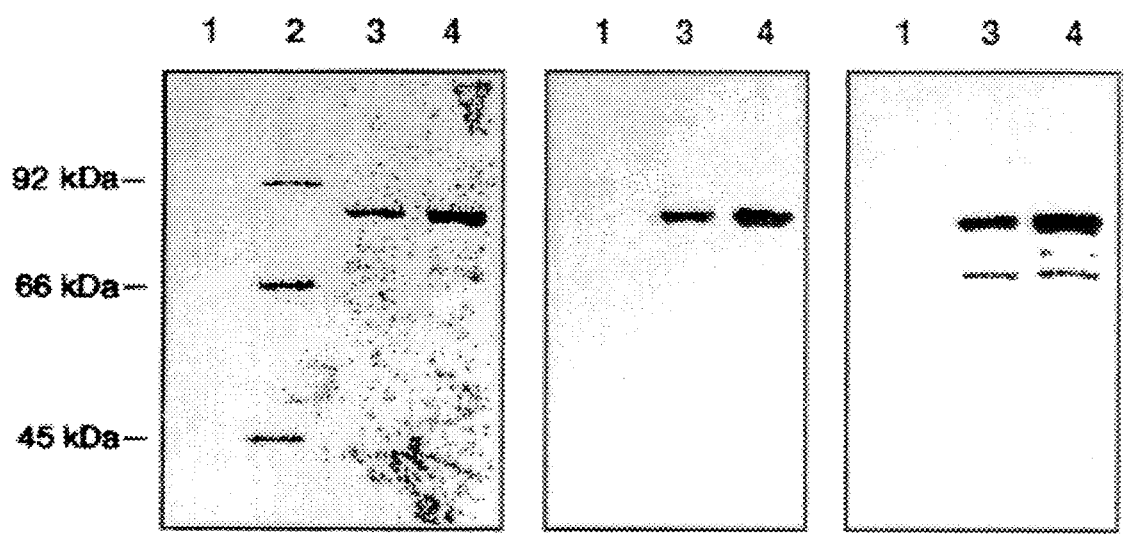

FIG. 4: Characterization of the material secreted after 4 days of culture (Erlenmeyers) of the strain CBS 293.91 transformed with plasmids pYG1266(plasmid for the expression of a chimera of the HSA-G.CSF type), and pKan707 (control plasmid). In this experiment, the results in diagrams A, B and C have been migrated on the same gel (SDS-PAGE 8.5%) and then treated separately.

A, Coomassie blue staining; molecular weight standard (lane 2); supernatant equivalent to 100 μl of the culture transformed with plasmids pKan707 in YPL medium (lane 1), or pYG1266 in YPD (lane 3) or YPL (lane 4) medium.

B, immunological characterization of the material secreted after the use of primary antibodies directed against human G-CSF: same legend as in A.

C, immunological characterization of the material secreted after the use of primary antibodies directed against human albumin: same legend as in A.

FIG. 5: Nucleotide sequence (SEQ ID NO: 3) and deduced amino acid sequence (SEQ ID NO: 4) of the HindIII restriction fragment of plasmid pYG1301 (chimera G.CSF-$Gly_4$-HSA). The solid arrows indicate the end of the HSA "pre" and "pro" regions. The ApaI, SstI (SacI) and MstII restriction sites are underlined. The G.CSF (174 residues) and HSA (585 residues) domains are separated by the synthetic linker GGGG. The numbering of the amino acids corresponds to the mature chimeric G.CSF-Gly4-HSA protein (763 residues). The nucleotide sequence lying between the translation termination codon and the HindIII site originates from HSA complementary DNA (cDNA) as described in Patent Application EP 361,991.

Figure 6A:
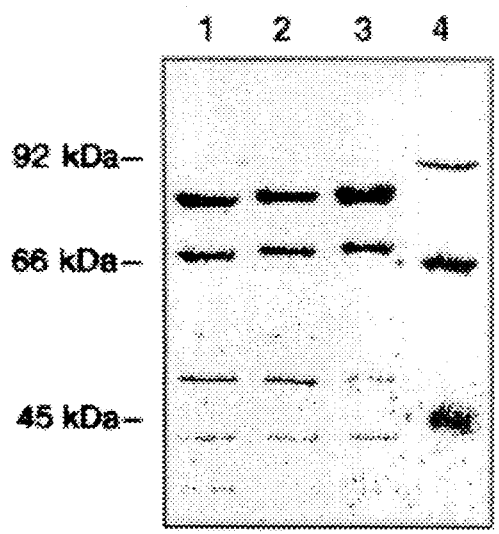
Figure 6B:
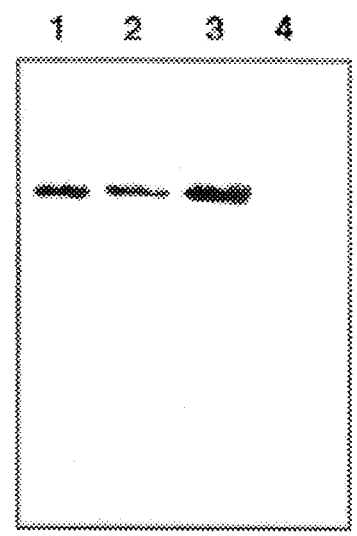

FIG. 6: Characterization of the material secreted after 4 days of culture (Erlenmeyers, in YPD medium) of the strain CBS 293.91 transformed with plasmids pYG1267 (chimera HSA-G.CSF), pYG1303 (chimera G.CSF-$Gly_4$-HSA) and pYG1352 (chimera HSA-$Gly_4$-G.CSF) after migration on SDS-PAGE 8.5% gel.

A, Coomassie blue staining; supernatant equivalent to 100 μl of the culture transformed with plasmids pYG1303 (lane 1 ), pYG1267 (lane 2) or pYG1352 (lane 3); molecular weight standard (lane 4).

B, immunological characterization of the material secreted after the use of primary antibodies directed against human G-CSF: same legend as in A.

Figure 7:
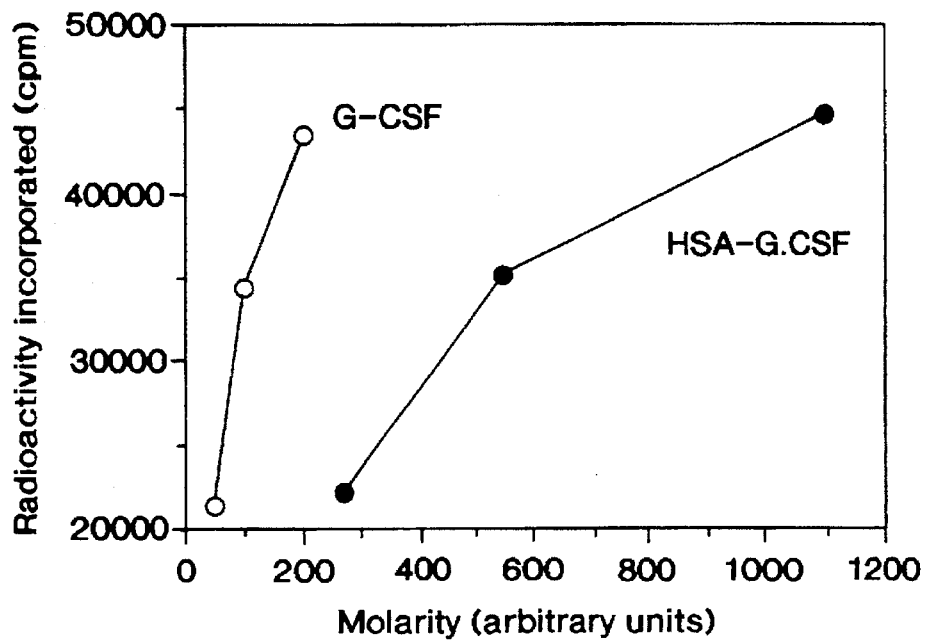

FIG. 7: Activity with respect to in vitro cell proliferation of the murine line NFS60. The radioactivity ([$^3$H]thymidine) incorporated in the cell nuclei after 6 hours of incubation is shown as ordinates (cpm); the amount of product shown as abscissae is expressed in molarity (arbitrary units).

Figure 8:
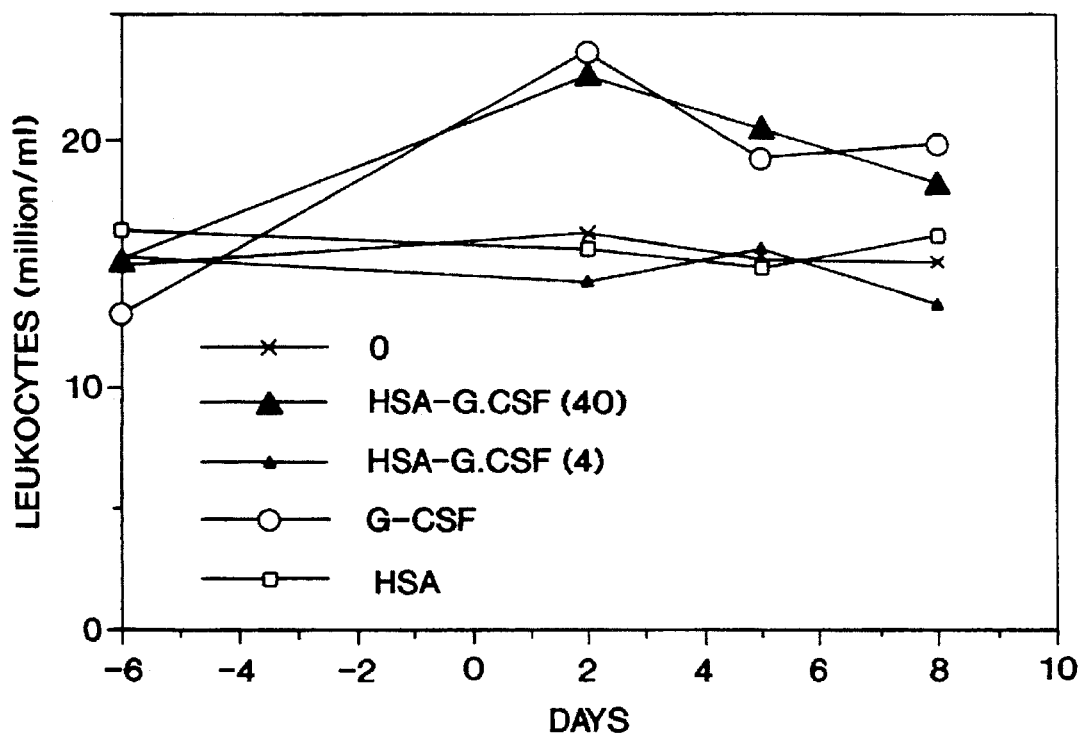

FIG. 8: Activity with respect to in vivo granulopoiesis in rats. The number of neutrophils (mean of 7 animals) is shown as ordinates as a function of time. The products tested are the chimera HSA-G.CSF (pYG1266, 4 or 40 mg/rat/day), reference G-CSF (10 mg/rat/day), recombinant HSA purified from Kluyveromyces lactis supernatant (rHSA, 30 mg/rat/day, see EP 361,991) or physiological saline.

EXAMPLES

GENERAL CLONING TECHNIQUES

The methods traditionally used in molecular biology, such as preparative extractions of plasmid DNA, caesium chloride gradient centrifugation of plasmid DNA, agarose or acrylamide gel electrophoresis, purification of DNA fragments by electroelution, protein extraction with phenol or phenol/chloroform, ethanol or isopropanol precipitation of DNA in a saline medium, transformation in Escherichia coil, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Restriction enzymes were supplied by New England Biolabs (Biolabs), Bethesda Research Laboratories (BRL) or Amersham, and are used according to the suppliers' recommendations.

pBR322 and pUC type plasmids and phages of the M13 series are of commercial origin (Bethesda Research Laboratories).

For the ligations, the DNA fragments are separated according to their size by agarose or acrylamide gel electrophoresis, extracted with phenol or with a phenol/chloroform mixture, precipitated with ethanol and then incubated in the presence of phage T4 DNA ligase (Biolabs) according to the suppliers recommendations.

The filling in of 5' protruding ends is performed with the Klenow fragment of E. coli DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Synthetic oligodeoxynucleotide-directed in vitro mutagenesis is performed according to the method developed by Taylor et el. [Nucleic Acids Res. 13 (1985) 8749–8764] using the kit distributed by Amersham.

The enzymatic amplification of DNA fragments by the so-called PCR [Polymerase-catalyzed Chain Reaction, Saiki R. K. et al., Science 230 (1985) 1350–1354; Mullis K. B. and Faloona F. A., Meth. Enzym. 155 (1987) 335–350] is performed using a DNA thermal cycler (Perkin Elmer Cetus) according to the manufacturer's specifications.

The verification of nucleotide sequences is performed by the method developed by Sanger et al. [Proc. Natl. Acad. Sci. USA, 74 (1977) 5463–5467] using the kit distributed by Amersham.

Transformations of K. lactis with the DNA of the plasmids for the expression of the proteins of the present invention are performed by any technique known to a person skilled in the art, an example of which is given in the text.

Except where otherwise stated, the bacterial strains used are E. coli MC1060 (laclPOZYA, X74, galU, galK, strA'), or E. coli TG1 (lac, proA,B, supE, thi, hsdD5 /FtraD36, proA+B$^+$, laclq, lacZ, M15).

The yeast strains used belong to budding yeasts, and more especially to yeasts of the genus Kluyveromyces. The strain K. lactis MW98-8C (a, uraA, arg, lys, K$^+$, pKD1$^-$) and K. lactis CBS 293.91 were used especially; a sample of the strain MW98-8C was deposited on 16th September, 1988 at the Centraalbureau voor Schimmelkulturen (CBS) in Baarn (Netherlands), where it was registered under the number CBS 579.88.

Yeast strains transformed with the expression plasmids coding for the proteins of the present invention are cultured in Erlenmeyers or in 21 pilot fermenters (SETRIC, France) at 28° C. in rich medium (YPD: 1% yeast extract, 2% Bactopeptone, 2% glucose; or YPL: 1% yeast extract, 2% Bactopeptone, 2% lactose) with constant stirring.

EXAMPLE 1: CONSTRUCTION OF AN MSTII-HINDIII RESTRICTION FRAGMENT INCLUDING THE MATURE PORTION OF HUMAN G-CSF

An MstII-HindIII restriction fragment including the mature form of human G-CSF is generated, for example, according to the following strategy: a KpnI-HindIII restriction fragment is first obtained by the PCR enzymatic amplification technique using the oligodeoxynucleotides Sq2291 (5'-CAAGGATCCAAGCTTCAGGGCTGCGCAAGGTG GCGTAG-3' (SEQ ID NO: 6), the HindIII site is underlined) and Sq2292 (5'-CGGGGTACCTTAGGCTTAACCCCCC TGGGCCCTGCCAGC-3' (SEQ ID NO: 7), the KpnI site is underlined) as primer on plasmid BBG13 serving as template. Plasmid BBG13 contains the gene coding for the B form (174 amino acids) of mature human G-CSF, obtained from Bdtish Bio-technology Limited, Oxford, England. The enzymatic amplification product of approximately 550 nucleotides is then digested with the restriction enzymes KpnI and HindIII and cloned into the vector pUC19 cut with the same enzymes, thereby generating the recombinant plasmid pYG1255. This plasmid is the source of an MstII-HindIII restriction fragment, the sequence of which is included in that of FIG. 1. An MstII-HindIII restriction fragment coding for the same polypeptide sequence may also be generated by the PCR amplification technique from the corresponding cDNAs, the sequence of which is known [Nagata S. et al., EMBO J. 5 (1986) 575–581 ]. These cDNAs may be isolated by the techniques of a person skilled in the art, for example using the kit distributed by Amersham, from a human cell line expressing G-CSF, and for example the human carcinoma cell line CHU-2 [Nagata et al., Nature 319 (1986) 415–418].

It can also be desirable to insert a peptide linker between the HSA portion and G-CSF, for example to permit a better functional presentation of the transducing portion. An MstII-HindIII restriction fragment is, for example, generated by substitution of the MstII-ApaI fragment of FIG. 1 by the oligodeoxynucleotides Sq2742 (5'-TTAGGCTTAGGTGGTGGCGGT ACCCCCCTGGGCC-3' (SEQ ID NO: 8), the codons coding for the glycine residues of this particular linker are underlined) and Sq2741 (5'-CAGGGGGGTACCGCCACCACCTAAGCC-3' (SEQ ID NO: 9)), which form, on pairing, an MstII-ApaI fragment. Plasmid pYG$^{1336}$ thus generated hence contains an MstII- HindIII restriction fragment, the sequence of which is identical to that of FIG. 1 except for the MstII-ApaI fragment.

EXAMPLE 2: TRANSLATIONALLY IN-FRAME FUSIONS BETWEEN HSA AND HUMAN G-CSF

E.2.1. Translational fusion of the HSA-G.CSF type

Plasmid pYG404 is described in Patent Application EP 361,991. This plasmid contains a HindIII restriction fragment coding for the prepro-HSA gene preceded by the 21 nucleotides naturally present immediately upstream of the translation initiation ATG of the PGK gene of *S. cerevisiae*. More especially; this fragment contains a HindIII-MstII restriction fragment corresponding to the whole of the gene coding for prepro-HSA except for the three most C-terminal amino acids (leucine-glycine-leucine residues). Ligation of this fragment with the MstII-HindIII fragment of plasmid pYG1255 makes it possible to generate the HindIII fragment of plasmid pYG1259 which codes for a chimeric protein in which the B form of mature G-CSF is positioned by genetic coupling translationally in-frame at the C-terminal end of the HSA molecule. The nucleotide sequence of this restriction fragment is given in FIG. 1, together with the polypeptide sequence of the corresponding chimera (HSA-G.CSF, see FIG. 2, diagram A).

A HindIII restriction fragment Which is identical except for the MstII-ApaI fragment may also be readily generated, and which codes for a chimeric protein in which the B form of mature G-CSF is positioned by genetic coupling translationally in-frame at the C-terminal end of the HSA molecule and of a particular peptide linker. For example, this linker consists of 4 glycine residues in the HindIII fragment of plasmid pYG1336 (chimera HSA-Gly$_4$-G.CSF, see FIG. 2, diagram A).

E.2.2. Translational fusion of the G.CSF-HSA type

In a particular embodiment, the combined techniques of directed mutagenesis and PCR amplification make it possible to construct hybrid genes coding for a chimeric protein (FIG. 2, diagram B) resulting from the translational coupling between a signal peptide (and for example the HSA prepro region), a sequence including a gene having G-CSF activity and the mature form of HSA or one of its molecular variants. These hybrid genes are preferably flanked at the 5' end of the translation initiation ATG and at the 3' end of the translation termination codon by HindIII restriction sites. For example, the oligodeoxynucleotide Sq2369 (5'-GTTCTACGCCACCTTGCGC AGCCCGGTGGAGGCG GTGATGCACACAAGAGTGAGGTTGCTCATCGG-3' (SEQ ID NO: 10), the underlined residues (optional) correspond in this particular chimera to a peptide linker composed of 4 glycine residues) enables the mature form of human G-CSF of plasmid BBG13 to be placed by directed mutagenesis immediately upstream of the mature form of HSA, thereby generating intermediate plasmid A. Similarly, the use of the oligodeoxynucleotide Sq2338 [5'-CAGGGAGCTGGCAGGGCCCAGGGGGTTCGACGAA ACACACCCCTGGAATAAGCCGAGCT-3' (SEQ ID NO: 11, non-coding strand), the nucleotides complementary to the nucleotides coding for the first N-terminal residues of the mature form of human G-CSF are underlined] enables the HSA prepro region to be coupled by directed mutagenesis in the translational reading frame immediately upstream of the mature form of human G-CSF, thereby generating intermediate plasmid B. The HindIII fragment of FIG. 5 is then generated by combining the HindIII-SstI fragment of plasmid B (junction of HSA prepro region+N-terminal fragment of mature GCSF, with the SstI-HindIII fragment of plasmid A [mature G-CSF-(glycine)$_{x4}$-mature HSA junction]. Plasmid pYG1301 contains this particular HindIII restriction fragment coding for the chimera G.CSF-Gly$_4$-HSA fused immediately downstream of the HSA prepro region.

E.2.3. Translational fusion of the G.CSF-HSA-G.CSF type

These same techniques of directed mutagenesis and DNA amplification in vitro enable hybrid genes to be constructed in which a sequence coding for G-CSF activity is coupled to the N- and C-terminal ends of HSA or one of its molecular variants (FIG. 2, diagram C). These hybrid genes are preferably flanked at the 5' end of the translation initiation ATG and at the 3' end of the translation termination codon by HindIII restriction sites.

EXAMPLE 3: CONSTRUCTION OF EXPRESSION PLASMIDS

The chimeric proteins of the preceding examples may be expressed in yeasts from regulable or constitutive functional promoters such as, for example, those present in plasmids pYG105 (LAC4 promoter of *Kluyveromyces lactis*), pYG106 (PGK promoter of *Saccharomyces cerevisiae*) and pYG536 (PHO5 promoter of *S. cerevisiae*), or hybrid promoters such as those carried by the plasmids described in Patent Application EP 361,991.

For example, the HindIII restriction fragment of pYG1259 is cloned in the productive orientation into the HindIII restriction site of the expression plasmid pYG105, thereby generating the expression plasmid pYG1266 (FIG. 3). Plasmid pYG105 corresponds to plasmid pKan707 described in Patent Application EP 361,991 in which the HindIII restriction site has been destroyed by directed mutagenesis (oligodeoxynucleotide Sq1053: 5'-GAAATGCATAAGCTCTTGCCATTCTCACCG-3' (SEQ ID NO: 12)), and the SalI-SacI fragment of which coding for the URA3 gene has been replaced by a SalI-SacI restriction fragment containing the LAC4 promoter (in the form of a SalI-HindIII fragment) and the terminator of the PGK gene of *S. cerevisiae* (in the form of a HindIII-SacI fragment). Plasmid pYG105 is mitotically very stable in the absence of geneticin (G418), and enables the chimetic protein to be expressed from the LAC4 promoter of *K. lactis*, in particular when the carbon source is lactose. In another exemplification, cloning of the HindIII restriction fragment of plasmid pYG1259 in the productive orientation into the HindIII site of plasmid pYG106 generates the expression plasmid pYG1267. Plasmids pYG1266 and pYG1267 are isogenic with one another, except for the SalI-HindIII restriction fragment coding for the LAC4 promoter of *K. lactis* (plasmid pYG1266) or the PGK promoter of *S. cerevisiae* (plasmid pYG1267).

In another exemplification, cloning of the HindIII restriction fragment of plasmid pYG1336 (chimera HSA-Gly$_4$-G.CSF, see E.2.1.) in the productive orientation into the HindIII site of plasmids pYG105 and pYG106 generates the expression plasmids pYG1351 and pYG1352, respectively.

Likewise, cloning of the HindIII restriction fragment of plasmid pYG1301 (chimera G.CSF-Gly$_4$-HSA, see E.2.2.) in the productive orientation into the HindIII site of plasmids pYG105 and pYG106 generates the expression plasmids pYG1302 and pYG1303, respectively.

EXAMPLE 4: TRANSFORMATION OF YEASTS

Transformation of yeasts belonging to the genus Kluyveromyces, and especially *K. lactis* strains MW98-8C and CBS 293.91, is performed, for example, by the technique of treatment of whole cells with lithium acetate [Ito H: et al., *J. Bacteriol.* 153 (1983) 163–168], adapted as follows. Cell growth takes place at 28° C. in 50 ml of YPD medium, with stirring and to an optical density at 600 nm ($OD_{600}$) of between 0.6 and 0.8; the cells are harvested by low speed centrifugation, washed in sterile TE solution (10 mM Tris-HCl pH 7.4; 1 mM EDTA), resuspended in 3–4 ml of lithium acetate (0.1M in TE) to obtain a cell density of approximately $2 \times 10^8$ cells/ml, and then incubated at 30° C. for 1 hour with moderate stirring. 0.1 ml aliquots of the resulting suspension of competent cells are incubated at 30° C. for 1 hour in the presence of DNA and at a final concentration of 35% of polyethylene glycol ($PEG_{4000}$, Sigma). After a 5-minute thermal shock at 42° C., the cells are washed twice, resuspended in 0.2 ml of sterile water and incubated for 16 hours at 28° C. in 2 ml of YPD medium to permit the phenotypic expression of the ORFI-APH fusion expressed under the control of the $P_{k1}$ promoter; 200 μl of the cell suspension are then plated out on selective YPD dishes (G418, 200 μg/ml). The dishes are incubated at 28° C. and the transformants appear after 2 to 3 days of cell growth.

EXAMPLE 5: SECRETION OF CHIMERAS

After selection on rich medium supplemented with G418, the recombinant clones are tested for their capacity to secrete the mature form of the proteins which are chimeras between HSA and G-CSF. A few clones corresponding to *K. lactis* strain CBS 293.91 transformed with plasmids pYG1266 or pYG1267 (HSA-G.CSF), pYG1302 or pYG1303 (G.CSF-Gly$_4$-HSA) or alternatively pYG1351 or pYG1352 (HSA-Gly4-G.CSF) are incubated in selective complete liquid medium at 28° C. The cell supernatants are then tested after electrophoresis on 8.5% acrylamide gel, either directly by staining the acrylamide gel with Coomassie blue (FIG. 4, diagram A), or after immunoblotting using as primary antibodies rabbit polyclonal antibodies directed specifically against human G-CSF or against HSA. In the immunological detection experiments, the nitrocellulose filter is first incubated in the presence of the specific antibody, washed several times, incubated in the presence of biotinylated goat anti-rabbit antibodies and then incubated in the presence of an avidin-peroxidase complex using the "ABC kit" distributed by Vectastain (Biosys S. A., Compiègne, France). The immunological reaction is then visualized by adding 3,3-diaminobenzidine tetrahydrochloride (Prolabo) in the presence of hydrogen peroxide, according to the supplier's recommendations. The results in FIG. 4 demonstrate that the HSA-G.CSF hybrid protein is recognized both by antibodies directed against human albumin (diagram C) and human G-CSF (diagram B). The results in FIG. 6 indicate that the chimera HSA-Gly4-G.CSF (lane 3) is especially well secreted by Kluyveromyces yeast, possibly because the presence of the peptide linker between HSA portion and G-CSF portion is more favourable to an independent folding of these portions on transit of the chimera into the secretory pathway. Furthermore, the N-terminal fusion (G.CSF-Gly$_4$-HSA) is also secreted by Kluyveromyces yeast (FIG. 6, lane 1).

EXAMPLE 6: PURIFICATION AND MOLECULAR CHARACTERIZATION OF THE SECRETED PRODUCTS

After centrifugation of a culture of the strain CBS 293.91 transformed with the expression plasmids according to Example 3, the culture supernatant is passed through a 0.22 mm filter (Millipore) and then concentrated by ultrafiltration (Amicon) using a membrane whose discrimination threshold lies at 30 kDa. The concentrate obtained is then adjusted to 50 mM Tris-HCl from a 1M stock solution of Tris-HCl (pH 6), and thereafter applied in 20-ml fractions to an ion exchange column (5 ml) (Q Fast Flow, Pharmacia) equilibrated in the same buffer. The chimeric protein is then eluted from the column with an NaCl gradient (0 to 1M). The fractions containing the chimeric protein are then pooled and dialysed against a 50 mM Tds-HCI solution (pH 6) and reapplied to a Q Fast Flow column (1 ml) equilibrated in the same buffer. After elution from the column, the fractions containing the protein are pooled, dialysed against water and lyophilized before characterization: for example, sequencing (Applied Biosystem) of the HSA-G.CSF protein secreted by the yeast CBS 293.91 gives the expected N-terminal sequence of HSA (Asp-Ala-His . . . ), demonstrating a correct maturation of the chimera on the immediately C-terminal side of the doublet of Arg—Arg residues of the HSA "pro" region (FIG. 1).

EXAMPLE 7: BIOLOGICAL ACTIVITY OF THE CHIMERAS BETWEEN HSA AND G-CSF

E.7.1. In vitro biological activity

The chimeras purified according to Example 6 are tested for their capacity to permit in vitro proliferation of the IL3-dependent murine line NFS60, by measuring the incorporation of tritiated thymidine essentially according to the protocol described by Tsuchiya et al. [Proc. Natl. Acad. Sci. (1986) 83 7633]. For each chimera, measurements are carried out between 3 and 6 times in a three-point test (three dilutions of the product) in a region or the relationship between amount of active product and incorporation of labelled thymidine (Amersham) is linear. In each microtitration plate, the activity of a reference product consisting of recombinant human G-CSF expressed in mammalian cells is also systematically incorporated. The results in FIG. 7 demonstrate that the chimera HSA-G.CSF (pYG1266) secreted by Kluyveromyces yeast is capable in vitro of transducing a cell proliferation signal for the NFS60 line. In this particular case, the specific activity (cpm/molarity) of the chimera is approximately one seventh that of the reference G-CSF (not coupled).

E.7.2. In vivo activity

The stimulatory activity of the HSNG-CSF chimeras with respect to in vivo granulopoiesis is tested after subcutaneous injection in rats (Sprague-Dawley/CD, 250–300 g, 8–9 weeks) and compared with that of the reference G-CSF expressed from mammalian cells. Each product, tested on the basis of 7 animals, is injected subcutaneously into the dorsoscapular region on the basis of 100 ml over 7 consecutive days (D1–D7). 500 ml of blood are collected on days D-6, D2 (before the 2nd injection), D5 (before the 5th injection) and D8, and a blood count is performed. In this test, the specific activity (neutropoiesis units/mole injected) of the chimera HSA-G.CSF (pYG1266) is identical to that of the reference G-CSF (FIG. 8). Since this particular chimera possesses in vitro a specific activity one seventh that of the reference G-CSF (FIG. 7), it is hence demonstrated that the genetic coupling of G-CSF to HSA favourably modifies its pharmacokinetic properties.

I claim:

1. Recombinant polypeptide comprising G-CSF coupled to albumin or a natural variant of albumin, wherein said G-CSF comprises residues Thr586-Pro759 of the sequence given in FIG. 1 (SEQ ID NO:2 residues Thr610-Pro783).

2. Polypeptide according to claim 1 wherein the G-CSF is coupled to the C-terminal end of the albumin or natural variant of albumin.

3. Polypeptide according to claim 1 wherein the G-CSF is coupled to the N-terminal end of the albumin or natural variant of albumin.

4. Nucleic acid coding for a polypeptide comprising G-CSF coupled to albumin or a natural variant of albumin, wherein said G-CSF comprises residues Thr586-Pro759 of the sequence given in FIG. 1 (SEQ ID NO:2 residues Thr610-Pro783).

5. Nucleic Acid according to claim 4 comprising a nucleotide sequence creating a leader sequence enabling the polypeptide expressed to be secreted.

6. Expression cassette comprising nucleic acid according to claim 4 operably linked to a transcription initiation region.

7. Self-replicating plasmid containing an expression cassette according to claim 6.

8. Recombinant eukaryotic or prokaryotic cell comprising a nucleic acid according to claim 4.

9. Recombinant cell according to claim 8, selected from the group consisting of a yeast, an animal cell, a fungus and a bacterium.

10. Recombinant cell according to claim 9, wherein said cell is a yeast.

11. Recombinant cell according to claim 10, wherein said yeast is of the genus Saccharomyces or Kluyveromyces.

12. Method for preparing a polypeptide comprising culturing a recombinant cell according to claim 8 under conditions for expression.

13. Pharmaceutical composition comprising one or more polypeptides according to claim 1 in a pharmaceutically effective vehicle.

* * * * *

UNITED STATES PATENT AND TRADEMARK OFFICE
CERTIFICATE OF CORRECTION

PATENT NO.    : 5,665,863
DATED         : September 9, 1997
INVENTOR(S)   : Patrice Yeh It is certified that error appears in the above-identified patent and that said Letters Patent is hereby corrected as shown below:

On the title page, please change

[22]  PCT Filed:  Jan. 28, 1993

Signed and Sealed this

Eighth Day of September, 1998

Attest:

BRUCE LEHMAN

Attesting Officer                Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2382 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 26..2377

( i x ) FEATURE:
        ( A ) NAME/KEY: misc_feature
        ( B ) LOCATION: 1842..1848
        ( D ) OTHER INFORMATION: /label=MstII-site ( i x ) FEATURE:
        ( A ) NAME/KEY: misc_feature
        ( B ) LOCATION: 1861..1866
        ( D ) OTHER INFORMATION: /label=ApaI-site ( i x ) FEATURE:
        ( A ) NAME/KEY: misc_feature
        ( B ) LOCATION: 2035..2040
        ( D ) OTHER INFORMATION: /label=SstI-site ( x i ) SEQUENCE DESCRIPTION: SEQ ID NO:1:

```
AAGCTTTACA ACAAATATAA AAACA ATG AAG TGG GTA ACC TTT ATT TCC CTT        52
                              Met Lys Trp Val Thr Phe Ile Ser Leu
                               1               5

CTT TTT CTC TTT AGC TCG GCT TAT TCC AGG GGT GTG TTT CGT CGA GAT       100
Leu Phe Leu Phe Ser Ser Ala Tyr Ser Arg Gly Val Phe Arg Arg Asp
 10              15                  20                  25

GCA CAC AAG AGT GAG GTT GCT CAT CGG TTT AAA GAT TTG GGA GAA GAA       148
Ala His Lys Ser Glu Val Ala His Arg Phe Lys Asp Leu Gly Glu Glu
             30                  35                  40

AAT TTC AAA GCC TTG GTG TTG ATT GCC TTT GCT CAG TAT CTT CAG CAG       196
Asn Phe Lys Ala Leu Val Leu Ile Ala Phe Ala Gln Tyr Leu Gln Gln
             45                  50                  55

TGT CCA TTT GAA GAT CAT GTA AAA TTA GTG AAT GAA GTA ACT GAA TTT       244
Cys Pro Phe Glu Asp His Val Lys Leu Val Asn Glu Val Thr Glu Phe
         60                  65                  70

GCA AAA ACA TGT GTT GCT GAT GAG TCA GCT GAA AAT TGT GAC AAA TCA       292
Ala Lys Thr Cys Val Ala Asp Glu Ser Ala Glu Asn Cys Asp Lys Ser
     75                  80                  85

CTT CAT ACC CTT TTT GGA GAC AAA TTA TGC ACA GTT GCA ACT CTT CGT       340
Leu His Thr Leu Phe Gly Asp Lys Leu Cys Thr Val Ala Thr Leu Arg
 90                  95                 100                 105

GAA ACC TAT GGT GAA ATG GCT GAC TGC TGT GCA AAA CAA GAA CCT GAG       388
Glu Thr Tyr Gly Glu Met Ala Asp Cys Cys Ala Lys Gln Glu Pro Glu
                    110                 115                 120

AGA AAT GAA TGC TTC TTG CAA CAC AAA GAT GAC AAC CCA AAC CTC CCC       436
Arg Asn Glu Cys Phe Leu Gln His Lys Asp Asp Asn Pro Asn Leu Pro
                125                 130                 135

CGA TTG GTG AGA CCA GAG GTT GAT GTG ATG TGC ACT GCT TTT CAT GAC       484
```

```
Arg Leu Val Arg Pro Glu Val Asp Val Met Cys Thr Ala Phe His Asp
    140         145                 150

AAT GAA GAG ACA TTT TTG AAA AAA TAC TTA TAT GAA ATT GCC AGA AGA    532
Asn Glu Glu Thr Phe Leu Lys Lys Tyr Leu Tyr Glu Ile Ala Arg Arg
    155                 160                 165

CAT CCT TAC TTT TAT GCC CCG GAA CTC CTT TTC TTT GCT AAA AGG TAT    580
His Pro Tyr Phe Tyr Ala Pro Glu Leu Leu Phe Phe Ala Lys Arg Tyr
170             175                 180                 185

AAA GCT GCT TTT ACA GAA TGT TGC CAA GCT GCT GAT AAA GCT GCC TGC    628
Lys Ala Ala Phe Thr Glu Cys Cys Gln Ala Ala Asp Lys Ala Ala Cys
                190                 195                 200

CTG TTG CCA AAG CTC GAT GAA CTT CGG GAT GAA GGG AAG GCT TCG TCT    676
Leu Leu Pro Lys Leu Asp Glu Leu Arg Asp Glu Gly Lys Ala Ser Ser
            205                 210                 215

GCC AAA CAG AGA CTC AAG TGT GCC AGT CTC CAA AAA TTT GGA GAA AGA    724
Ala Lys Gln Arg Leu Lys Cys Ala Ser Leu Gln Lys Phe Gly Glu Arg
        220                 225                 230

GCT TTC AAA GCA TGG GCA GTA GCT CGC CTG AGC CAG AGA TTT CCC AAA    772
Ala Phe Lys Ala Trp Ala Val Ala Arg Leu Ser Gln Arg Phe Pro Lys
    235                 240                 245

GCT GAG TTT GCA GAA GTT TCC AAG TTA GTG ACA GAT CTT ACC AAA GTC    820
Ala Glu Phe Ala Glu Val Ser Lys Leu Val Thr Asp Leu Thr Lys Val
250                 255                 260                 265

CAC ACG GAA TGC TGC CAT GGA GAT CTG CTT GAA TGT GCT GAT GAC AGG    868
His Thr Glu Cys Cys His Gly Asp Leu Leu Glu Cys Ala Asp Asp Arg
                270                 275                 280

GCG GAC CTT GCC AAG TAT ATC TGT GAA AAT CAA GAT TCG ATC TCC AGT    916
Ala Asp Leu Ala Lys Tyr Ile Cys Glu Asn Gln Asp Ser Ile Ser Ser
            285                 290                 295

AAA CTG AAG GAA TGC TGT GAA AAA CCT CTG TTG GAA AAA TCC CAC TGC    964
Lys Leu Lys Glu Cys Cys Glu Lys Pro Leu Leu Glu Lys Ser His Cys
        300                 305                 310

ATT GCC GAA GTG GAA AAT GAT GAG ATG CCT GCT GAC TTG CCT TCA TTA   1012
Ile Ala Glu Val Glu Asn Asp Glu Met Pro Ala Asp Leu Pro Ser Leu
    315                 320                 325

GCT GCT GAT TTT GTT GAA AGT AAG GAT GTT TGC AAA AAC TAT GCT GAG   1060
Ala Ala Asp Phe Val Glu Ser Lys Asp Val Cys Lys Asn Tyr Ala Glu
330                 335                 340                 345

GCA AAG GAT GTC TTC CTG GGC ATG TTT TTG TAT GAA TAT GCA AGA AGG   1108
Ala Lys Asp Val Phe Leu Gly Met Phe Leu Tyr Glu Tyr Ala Arg Arg
                350                 355                 360

CAT CCT GAT TAC TCT GTC GTA CTG CTG CTG AGA CTT GCC AAG ACA TAT   1156
His Pro Asp Tyr Ser Val Val Leu Leu Leu Arg Leu Ala Lys Thr Tyr
            365                 370                 375

GAA ACC ACT CTA GAG AAG TGC TGT GCC GCT GCA GAT CCT CAT GAA TGC   1204
Glu Thr Thr Leu Glu Lys Cys Cys Ala Ala Ala Asp Pro His Glu Cys
        380                 385                 390

TAT GCC AAA GTG TTC GAT GAA TTT AAA CCT CTT GTG GAA GAG CCT CAG   1252
Tyr Ala Lys Val Phe Asp Glu Phe Lys Pro Leu Val Glu Glu Pro Gln
    395                 400                 405

AAT TTA ATC AAA CAA AAT TGT GAG CTT TTT GAG CAG CTT GGA GAG TAC   1300
Asn Leu Ile Lys Gln Asn Cys Glu Leu Phe Glu Gln Leu Gly Glu Tyr
410                 415                 420                 425

AAA TTC CAG AAT GCG CTA TTA GTT CGT TAC ACC AAG AAA GTA CCC CAA   1348
Lys Phe Gln Asn Ala Leu Leu Val Arg Tyr Thr Lys Lys Val Pro Gln
                430                 435                 440

GTG TCA ACT CCA ACT CTT GTA GAG GTC TCA AGA AAC CTA GGA AAA GTG   1396
Val Ser Thr Pro Thr Leu Val Glu Val Ser Arg Asn Leu Gly Lys Val
            445                 450                 455

GGC AGC AAA TGT TGT AAA CAT CCT GAA GCA AAA AGA ATG CCC TGT GCA   1444
```

|  |  |  |  |  |  |  |  |  |  |  |  |  |  |  |  |
|---|---|---|---|---|---|---|---|---|---|---|---|---|---|---|---|
| Gly | Ser | Lys<br>460 | Cys | Cys | Lys | His | Pro<br>465 | Glu | Ala | Lys | Arg<br>470 | Met | Pro | Cys | Ala |

| GAA | GAC | TAT | CTA | TCC | GTG | GTC | CTG | AAC | CAG | TTA | TGT | GTG | TTG | CAT | GAG | 1492 |
|---|---|---|---|---|---|---|---|---|---|---|---|---|---|---|---|---|
| Glu | Asp<br>475 | Tyr | Leu | Ser | Val | Val<br>480 | Leu | Asn | Gln | Leu | Cys<br>485 | Val | Leu | His | Glu |  |

| AAA | ACG | CCA | GTA | AGT | GAC | AGA | GTC | ACC | AAA | TGC | TGC | ACA | GAA | TCC | TTG | 1540 |
|---|---|---|---|---|---|---|---|---|---|---|---|---|---|---|---|---|
| Lys<br>490 | Thr | Pro | Val | Ser | Asp | Arg<br>495 | Val | Thr | Lys | Cys<br>500 | Cys | Thr | Glu | Ser | Leu<br>505 |  |

| GTG | AAC | AGG | CGA | CCA | TGC | TTT | TCA | GCT | CTG | GAA | GTC | GAT | GAA | ACA | TAC | 1588 |
|---|---|---|---|---|---|---|---|---|---|---|---|---|---|---|---|---|
| Val | Asn | Arg | Arg | Pro<br>510 | Cys | Phe | Ser | Ala | Leu<br>515 | Glu | Val | Asp | Glu | Thr<br>520 | Tyr |  |

| GTT | CCC | AAA | GAG | TTT | AAT | GCT | GAA | ACA | TTC | ACC | TTC | CAT | GCA | GAT | ATA | 1636 |
|---|---|---|---|---|---|---|---|---|---|---|---|---|---|---|---|---|
| Val | Pro | Lys<br>525 | Glu | Phe | Asn | Ala | Glu<br>530 | Thr | Phe | Thr | Phe | His<br>535 | Ala | Asp | Ile |  |

| TGC | ACA | CTT | TCT | GAG | AAG | GAG | AGA | CAA | ATC | AAG | AAA | CAA | ACT | GCA | CTT | 1684 |
|---|---|---|---|---|---|---|---|---|---|---|---|---|---|---|---|---|
| Cys | Thr | Leu<br>540 | Ser | Glu | Lys | Glu | Arg<br>545 | Gln | Ile | Lys | Lys | Gln<br>550 | Thr | Ala | Leu |  |

| GTT | GAG | CTT | GTG | AAA | CAC | AAG | CCC | AAG | GCA | ACA | AAA | GAG | CAA | CTG | AAA | 1732 |
|---|---|---|---|---|---|---|---|---|---|---|---|---|---|---|---|---|
| Val | Glu<br>555 | Leu | Val | Lys | His | Lys<br>560 | Pro | Lys | Ala | Thr | Lys<br>565 | Glu | Gln | Leu | Lys |  |

| GCT | GTT | ATG | GAT | GAT | TTC | GCA | GCT | TTT | GTA | GAG | AAG | TGC | TGC | AAG | GCT | 1780 |
|---|---|---|---|---|---|---|---|---|---|---|---|---|---|---|---|---|
| Ala<br>570 | Val | Met | Asp | Asp | Phe<br>575 | Ala | Ala | Phe | Val | Glu<br>580 | Lys | Cys | Cys | Lys | Ala<br>585 |  |

| GAC | GAT | AAG | GAG | ACC | TGC | TTT | GCC | GAG | GAG | GGT | AAA | AAA | CTT | GTT | GCT | 1828 |
|---|---|---|---|---|---|---|---|---|---|---|---|---|---|---|---|---|
| Asp | Asp | Lys | Glu | Thr<br>590 | Cys | Phe | Ala | Glu | Glu<br>595 | Gly | Lys | Lys | Leu | Val<br>600 | Ala |  |

| GCA | AGT | CAA | GCT | GCC | TTA | GGC | TTA | ACC | CCC | TTG | GGC | CCT | GCC | AGC | TCC | 1876 |
|---|---|---|---|---|---|---|---|---|---|---|---|---|---|---|---|---|
| Ala | Ser | Gln | Ala<br>605 | Ala | Leu | Gly | Leu | Thr<br>610 | Pro | Leu | Gly | Pro | Ala<br>615 | Ser | Ser |  |

| CTG | CCC | CAG | AGC | TTC | CTG | CTC | AAG | TGC | TTA | GAG | CAA | GTG | AGG | AAG | ATC | 1924 |
|---|---|---|---|---|---|---|---|---|---|---|---|---|---|---|---|---|
| Leu | Pro | Gln | Ser<br>620 | Phe | Leu | Leu | Lys | Cys<br>625 | Leu | Glu | Gln | Val | Arg<br>630 | Lys | Ile |  |

| CAG | GGC | GAT | GGC | GCA | GCG | CTC | CAG | GAG | AAG | CTG | TGT | GCC | ACC | TAC | AAG | 1972 |
|---|---|---|---|---|---|---|---|---|---|---|---|---|---|---|---|---|
| Gln | Gly | Asp<br>635 | Gly | Ala | Ala | Leu | Gln<br>640 | Glu | Lys | Leu | Cys | Ala<br>645 | Thr | Tyr | Lys |  |

| CTG | TGC | CAC | CCC | GAG | GAG | CTG | GTG | CTG | CTC | GGA | CAC | TCT | CTG | GGC | ATC | 2020 |
|---|---|---|---|---|---|---|---|---|---|---|---|---|---|---|---|---|
| Leu<br>650 | Cys | His | Pro | Glu | Glu<br>655 | Leu | Val | Leu | Leu | Gly<br>660 | His | Ser | Leu | Gly | Ile<br>665 |  |

| CCC | TGG | GCT | CCC | CTG | AGC | TCC | TGC | CCC | AGC | CAG | GCC | CTG | CAG | CTG | GCA | 2068 |
|---|---|---|---|---|---|---|---|---|---|---|---|---|---|---|---|---|
| Pro | Trp | Ala | Pro | Leu<br>670 | Ser | Ser | Cys | Pro | Ser<br>675 | Gln | Ala | Leu | Gln | Leu<br>680 | Ala |  |

| GGC | TGC | TTG | AGC | CAA | CTC | CAT | AGC | GGC | CTT | TTC | CTC | TAC | CAG | GGG | CTC | 2116 |
|---|---|---|---|---|---|---|---|---|---|---|---|---|---|---|---|---|
| Gly | Cys | Leu | Ser<br>685 | Gln | Leu | His | Ser<br>690 | Gly | Leu | Phe | Leu | Tyr<br>695 | Gln | Gly | Leu |  |

| CTG | CAG | GCC | CTG | GAA | GGG | ATA | TCC | CCC | GAG | TTG | GGT | CCC | ACC | TTG | GAC | 2164 |
|---|---|---|---|---|---|---|---|---|---|---|---|---|---|---|---|---|
| Leu | Gln | Ala | Leu<br>700 | Glu | Gly | Ile | Ser<br>705 | Pro | Glu | Leu | Gly | Pro<br>710 | Thr | Leu | Asp |  |

| ACA | CTG | CAG | CTG | GAC | GTC | GCC | GAC | TTT | GCC | ACC | ACC | ATC | TGG | CAG | CAG | 2212 |
|---|---|---|---|---|---|---|---|---|---|---|---|---|---|---|---|---|
| Thr | Leu<br>715 | Gln | Leu | Asp | Val | Ala<br>720 | Asp | Phe | Ala | Thr | Thr<br>725 | Ile | Trp | Gln | Gln |  |

| ATG | GAA | GAA | CTG | GGA | ATG | GCC | CCT | GCC | CTG | CAG | CCC | ACC | CAG | GGT | GCC | 2260 |
|---|---|---|---|---|---|---|---|---|---|---|---|---|---|---|---|---|
| Met<br>730 | Glu | Glu | Leu | Gly | Met<br>735 | Ala | Pro | Ala | Leu | Gln<br>740 | Pro | Thr | Gln | Gly | Ala<br>745 |  |

| ATG | CCG | GCC | TTC | GCC | TCT | GCT | TTC | CAG | CGC | CGG | GCA | GGA | GGG | GTC | CTG | 2308 |
|---|---|---|---|---|---|---|---|---|---|---|---|---|---|---|---|---|
| Met | Pro | Ala | Phe | Ala<br>750 | Ser | Ala | Phe | Gln | Arg<br>755 | Arg | Ala | Gly | Gly | Val<br>760 | Leu |  |

| GTT | GCT | AGC | CAT | CTG | CAG | AGC | TTC | CTG | GAG | GTG | TCG | TAC | CGC | GTT | CTA | 2356 |
|---|---|---|---|---|---|---|---|---|---|---|---|---|---|---|---|---|
| Val | Ala | Ser | His<br>765 | Leu | Gln | Ser | Phe<br>770 | Leu | Glu | Val | Ser | Tyr<br>775 | Arg | Val | Leu |  |

| CGC | CAC | CTT | GCG | CAG | CCC | TGAAGCTT |  |  |  |  |  |  |  |  |  | 2382 |

Arg His Leu Ala Gln Pro
             780

(2) INFORMATION FOR SEQ ID NO:2:

(i) SEQUENCE CHARACTERISTICS:
        (A) LENGTH: 783 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
             20                  25                  30

His Arg Phe Lys Asp Leu Gly Glu Glu Asn Phe Lys Ala Leu Val Leu
         35                  40                  45

Ile Ala Phe Ala Gln Tyr Leu Gln Gln Cys Pro Phe Glu Asp His Val
     50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350
```

```
Met Phe Leu Tyr Glu Tyr Ala Arg Arg His Pro Asp Tyr Ser Val Val
        355                 360                 365
Leu Leu Leu Arg Leu Ala Lys Thr Tyr Glu Thr Thr Leu Glu Lys Cys
    370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
        435                 440                 445
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
        595                 600                 605
Leu Thr Pro Leu Gly Pro Ala Ser Ser Leu Pro Gln Ser Phe Leu Leu
    610                 615                 620
Lys Cys Leu Glu Gln Val Arg Lys Ile Gln Gly Asp Gly Ala Ala Leu
625                 630                 635                 640
Gln Glu Lys Leu Cys Ala Thr Tyr Lys Leu Cys His Pro Glu Glu Leu
                645                 650                 655
Val Leu Leu Gly His Ser Leu Gly Ile Pro Trp Ala Pro Leu Ser Ser
            660                 665                 670
Cys Pro Ser Gln Ala Leu Gln Leu Ala Gly Cys Leu Ser Gln Leu His
        675                 680                 685
Ser Gly Leu Phe Leu Tyr Gln Gly Leu Leu Gln Ala Leu Glu Gly Ile
    690                 695                 700
Ser Pro Glu Leu Gly Pro Thr Leu Asp Thr Leu Gln Leu Asp Val Ala
705                 710                 715                 720
Asp Phe Ala Thr Thr Ile Trp Gln Gln Met Glu Glu Leu Gly Met Ala
                725                 730                 735
Pro Ala Leu Gln Pro Thr Gln Gly Ala Met Pro Ala Phe Ala Ser Ala
            740                 745                 750
Phe Gln Arg Arg Ala Gly Gly Val Leu Val Ala Ser His Leu Gln Ser
        755                 760                 765
Phe Leu Glu Val Ser Tyr Arg Val Leu Arg His Leu Ala Gln Pro
```

( 2 ) INFORMATION FOR SEQ ID NO:3:

( i ) SEQUENCE CHARACTERISTICS:
        ( A ) LENGTH: 2455 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 26..2389

( i x ) FEATURE:
        ( A ) NAME/KEY: misc_feature
        ( B ) LOCATION: 106..111
        ( D ) OTHER INFORMATION: /label=ApaI-site ( i x ) FEATURE:
        ( A ) NAME/KEY: misc_feature
        ( B ) LOCATION: 280..285
        ( D ) OTHER INFORMATION: /label=SstI-site ( i x ) FEATURE:
        ( A ) NAME/KEY: misc_feature
        ( B ) LOCATION: 2376..2382
        ( D ) OTHER INFORMATION: /label=MstII-site ( i x ) FEATURE:
        ( A ) NAME/KEY: sig_peptide
        ( B ) LOCATION: 26..97

( i x ) FEATURE:
        ( A ) NAME/KEY: misc_feature
        ( B ) LOCATION: 620..631
        ( D ) OTHER INFORMATION: /label=polyGly-linker ( x i ) SEQUENCE DESCRIPTION: SEQ ID NO:3:

```
AAGCTTTACA ACAAATATAA AAACA ATG AAG TGG GTA ACC TTT ATT TCC CTT      52
                              Met Lys Trp Val Thr Phe Ile Ser Leu
                               1               5

CTT TTT CTC TTT AGC TCG GCT TAT TCC AGG GGT GTG TTT CGT CGA ACC     100
Leu Phe Leu Phe Ser Ser Ala Tyr Ser Arg Gly Val Phe Arg Arg Thr
 10              15                  20                      25

CCC CTG GGC CCT GCC AGC TCC CTG CCC CAG AGC TTC CTG CTC AAG TGC     148
Pro Leu Gly Pro Ala Ser Ser Leu Pro Gln Ser Phe Leu Leu Lys Cys
                 30                  35                  40

TTA GAG CAA GTG AGG AAG ATC CAG GGC GAT GGC GCA GCG CTC CAG GAG     196
Leu Glu Gln Val Arg Lys Ile Gln Gly Asp Gly Ala Ala Leu Gln Glu
             45                  50                  55

AAG CTG TGT GCC ACC TAC AAG CTG TGT CAC CCC GAG GAG CTG GTG CTG     244
Lys Leu Cys Ala Thr Tyr Lys Leu Cys His Pro Glu Glu Leu Val Leu
         60                  65                  70

CTC GGA CAC TCT CTG GGC ATC CCC TGG GCT CCC CTG AGC TCC TGC CCC     292
Leu Gly His Ser Leu Gly Ile Pro Trp Ala Pro Leu Ser Ser Cys Pro
     75                  80                  85

AGC CAG GCC CTG CAG CTG GCA GGC TGC TTG AGC CAA CTC CAT AGC GGC     340
Ser Gln Ala Leu Gln Leu Ala Gly Cys Leu Ser Gln Leu His Ser Gly
 90              95                 100                 105

CTT TTC CTC TAC CAG GGG CTC CTG CAG GCC CTG GAA GGG ATA TCC CCC     388
Leu Phe Leu Tyr Gln Gly Leu Leu Gln Ala Leu Glu Gly Ile Ser Pro
                110                 115                 120

GAG TTG GGT CCC ACC TTG GAC ACA CTG CAG CTG GAC GTC GCC GAC TTT     436
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Glu | Leu | Gly | Pro | Thr | Leu | Asp | Thr | Leu | Gln | Leu | Asp | Val | Ala | Asp | Phe |      |
|     |     |     | 125 |     |     |     | 130 |     |     |     |     |     | 135 |     |     |      |
| GCC | ACC | ACC | ATC | TGG | CAG | CAG | ATG | GAA | GAA | CTG | GGA | ATG | GCC | CCT | GCC | 484  |
| Ala | Thr | Thr | Ile | Trp | Gln | Gln | Met | Glu | Glu | Leu | Gly | Met | Ala | Pro | Ala |      |
|     |     | 140 |     |     |     |     | 145 |     |     |     |     | 150 |     |     |     |      |
| CTG | CAG | CCC | ACC | CAG | GGT | GCC | ATG | CCG | GCC | TTC | GCC | TCT | GCT | TTC | CAG | 532  |
| Leu | Gln | Pro | Thr | Gln | Gly | Ala | Met | Pro | Ala | Phe | Ala | Ser | Ala | Phe | Gln |      |
|     | 155 |     |     |     |     |     | 160 |     |     |     |     |     | 165 |     |     |      |
| CGC | CGG | GCA | GGA | GGG | GTC | CTG | GTT | GCT | AGC | CAT | CTG | CAG | AGC | TTC | CTG | 580  |
| Arg | Arg | Ala | Gly | Gly | Val | Leu | Val | Ala | Ser | His | Leu | Gln | Ser | Phe | Leu |      |
| 170 |     |     |     |     | 175 |     |     |     |     | 180 |     |     |     |     | 185 |      |
| GAG | GTG | TCG | TAC | CGC | GTT | CTA | CGC | CAC | CTT | GCG | CAG | CCC | GGT | GGA | GGC | 628  |
| Glu | Val | Ser | Tyr | Arg | Val | Leu | Arg | His | Leu | Ala | Gln | Pro | Gly | Gly | Gly |      |
|     |     |     |     | 190 |     |     |     |     | 195 |     |     |     |     | 200 |     |      |
| GGT | GAT | GCA | CAC | AAG | AGT | GAG | GTT | GCT | CAT | CGG | TTT | AAA | GAT | TTG | GGA | 676  |
| Gly | Asp | Ala | His | Lys | Ser | Glu | Val | Ala | His | Arg | Phe | Lys | Asp | Leu | Gly |      |
|     |     |     |     | 205 |     |     |     |     | 210 |     |     |     |     | 215 |     |      |
| GAA | GAA | AAT | TTC | AAA | GCC | TTG | GTG | TTG | ATT | GCC | TTT | GCT | CAG | TAT | CTT | 724  |
| Glu | Glu | Asn | Phe | Lys | Ala | Leu | Val | Leu | Ile | Ala | Phe | Ala | Gln | Tyr | Leu |      |
|     |     | 220 |     |     |     |     | 225 |     |     |     |     | 230 |     |     |     |      |
| CAG | CAG | TGT | CCA | TTT | GAA | GAT | CAT | GTA | AAA | TTA | GTG | AAT | GAA | GTA | ACT | 772  |
| Gln | Gln | Cys | Pro | Phe | Glu | Asp | His | Val | Lys | Leu | Val | Asn | Glu | Val | Thr |      |
|     | 235 |     |     |     |     | 240 |     |     |     |     | 245 |     |     |     |     |      |
| GAA | TTT | GCA | AAA | ACA | TGT | GTT | GCT | GAT | GAG | TCA | GCT | GAA | AAT | TGT | GAC | 820  |
| Glu | Phe | Ala | Lys | Thr | Cys | Val | Ala | Asp | Glu | Ser | Ala | Glu | Asn | Cys | Asp |      |
| 250 |     |     |     |     | 255 |     |     |     |     | 260 |     |     |     |     | 265 |      |
| AAA | TCA | CTT | CAT | ACC | CTT | TTT | GGA | GAC | AAA | TTA | TGC | ACA | GTT | GCA | ACT | 868  |
| Lys | Ser | Leu | His | Thr | Leu | Phe | Gly | Asp | Lys | Leu | Cys | Thr | Val | Ala | Thr |      |
|     |     |     |     | 270 |     |     |     |     | 275 |     |     |     |     | 280 |     |      |
| CTT | CGT | GAA | ACC | TAT | GGT | GAA | ATG | GCT | GAC | TGC | TGT | GCA | AAA | CAA | GAA | 916  |
| Leu | Arg | Glu | Thr | Tyr | Gly | Glu | Met | Ala | Asp | Cys | Cys | Ala | Lys | Gln | Glu |      |
|     |     |     | 285 |     |     |     |     | 290 |     |     |     |     | 295 |     |     |      |
| CCT | GAG | AGA | AAT | GAA | TGC | TTC | TTG | CAA | CAC | AAA | GAT | GAC | AAC | CCA | AAC | 964  |
| Pro | Glu | Arg | Asn | Glu | Cys | Phe | Leu | Gln | His | Lys | Asp | Asp | Asn | Pro | Asn |      |
|     |     | 300 |     |     |     |     | 305 |     |     |     |     | 310 |     |     |     |      |
| CTC | CCC | CGA | TTG | GTG | AGA | CCA | GAG | GTT | GAT | GTG | ATG | TGC | ACT | GCT | TTT | 1012 |
| Leu | Pro | Arg | Leu | Val | Arg | Pro | Glu | Val | Asp | Val | Met | Cys | Thr | Ala | Phe |      |
|     | 315 |     |     |     |     | 320 |     |     |     |     | 325 |     |     |     |     |      |
| CAT | GAC | AAT | GAA | GAG | ACA | TTT | TTG | AAA | AAA | TAC | TTA | TAT | GAA | ATT | GCC | 1060 |
| His | Asp | Asn | Glu | Glu | Thr | Phe | Leu | Lys | Lys | Tyr | Leu | Tyr | Glu | Ile | Ala |      |
| 330 |     |     |     |     | 335 |     |     |     |     | 340 |     |     |     |     | 345 |      |
| AGA | AGA | CAT | CCT | TAC | TTT | TAT | GCC | CCG | GAA | CTC | CTT | TTC | TTT | GCT | AAA | 1108 |
| Arg | Arg | His | Pro | Tyr | Phe | Tyr | Ala | Pro | Glu | Leu | Leu | Phe | Phe | Ala | Lys |      |
|     |     |     |     | 350 |     |     |     |     | 355 |     |     |     |     | 360 |     |      |
| AGG | TAT | AAA | GCT | GCT | TTT | ACA | GAA | TGT | TGC | CAA | GCT | GCT | GAT | AAA | GCT | 1156 |
| Arg | Tyr | Lys | Ala | Ala | Phe | Thr | Glu | Cys | Cys | Gln | Ala | Ala | Asp | Lys | Ala |      |
|     |     |     | 365 |     |     |     |     | 370 |     |     |     |     | 375 |     |     |      |
| GCC | TGC | CTG | TTG | CCA | AAG | CTC | GAT | GAA | CTT | CGG | GAT | GAA | GGG | AAG | GCT | 1204 |
| Ala | Cys | Leu | Leu | Pro | Lys | Leu | Asp | Glu | Leu | Arg | Asp | Glu | Gly | Lys | Ala |      |
|     |     | 380 |     |     |     |     | 385 |     |     |     |     | 390 |     |     |     |      |
| TCG | TCT | GCC | AAA | CAG | AGA | CTC | AAG | TGT | GCC | AGT | CTC | CAA | AAA | TTT | GGA | 1252 |
| Ser | Ser | Ala | Lys | Gln | Arg | Leu | Lys | Cys | Ala | Ser | Leu | Gln | Lys | Phe | Gly |      |
|     | 395 |     |     |     |     | 400 |     |     |     |     | 405 |     |     |     |     |      |
| GAA | AGA | GCT | TTC | AAA | GCA | TGG | GCA | GTA | GCT | CGC | CTG | AGC | CAG | AGA | TTT | 1300 |
| Glu | Arg | Ala | Phe | Lys | Ala | Trp | Ala | Val | Ala | Arg | Leu | Ser | Gln | Arg | Phe |      |
| 410 |     |     |     |     | 415 |     |     |     |     | 420 |     |     |     |     | 425 |      |
| CCC | AAA | GCT | GAG | TTT | GCA | GAA | GTT | TCC | AAG | TTA | GTG | ACA | GAT | CTT | ACC | 1348 |
| Pro | Lys | Ala | Glu | Phe | Ala | Glu | Val | Ser | Lys | Leu | Val | Thr | Asp | Leu | Thr |      |
|     |     |     |     | 430 |     |     |     |     | 435 |     |     |     |     | 440 |     |      |
| AAA | GTC | CAC | ACG | GAA | TGC | TGC | CAT | GGA | GAT | CTG | CTT | GAA | TGT | GCT | GAT | 1396 |

```
Lys Val His Thr Glu Cys Cys His Gly Asp Leu Leu Glu Cys Ala Asp
        445                 450                 455

GAC AGG GCG GAC CTT GCC AAG TAT ATC TGT GAA AAT CAA GAT TCG ATC      1444
Asp Arg Ala Asp Leu Ala Lys Tyr Ile Cys Glu Asn Gln Asp Ser Ile
        460                 465                 470

TCC AGT AAA CTG AAG GAA TGC TGT GAA AAA CCT CTG TTG GAA AAA TCC      1492
Ser Ser Lys Leu Lys Glu Cys Cys Glu Lys Pro Leu Leu Glu Lys Ser
        475                 480                 485

CAC TGC ATT GCC GAA GTG GAA AAT GAT GAG ATG CCT GCT GAC TTG CCT      1540
His Cys Ile Ala Glu Val Glu Asn Asp Glu Met Pro Ala Asp Leu Pro
490                 495                 500                 505

TCA TTA GCT GCT GAT TTT GTT GAA AGT AAG GAT GTT TGC AAA AAC TAT      1588
Ser Leu Ala Ala Asp Phe Val Glu Ser Lys Asp Val Cys Lys Asn Tyr
                510                 515                 520

GCT GAG GCA AAG GAT GTC TTC CTG GGC ATG TTT TTG TAT GAA TAT GCA      1636
Ala Glu Ala Lys Asp Val Phe Leu Gly Met Phe Leu Tyr Glu Tyr Ala
                525                 530                 535

AGA AGG CAT CCT GAT TAC TCT GTC GTA CTG CTG CTG AGA CTT GCC AAG      1684
Arg Arg His Pro Asp Tyr Ser Val Val Leu Leu Leu Arg Leu Ala Lys
            540                 545                 550

ACA TAT GAA ACC ACT CTA GAG AAG TGC TGT GCC GCT GCA GAT CCT CAT      1732
Thr Tyr Glu Thr Thr Leu Glu Lys Cys Cys Ala Ala Ala Asp Pro His
        555                 560                 565

GAA TGC TAT GCC AAA GTG TTC GAT GAA TTT AAA CCT CTT GTG GAA GAG      1780
Glu Cys Tyr Ala Lys Val Phe Asp Glu Phe Lys Pro Leu Val Glu Glu
570                 575                 580                 585

CCT CAG AAT TTA ATC AAA CAA AAT TGT GAG CTT TTT GAG CAG CTT GGA      1828
Pro Gln Asn Leu Ile Lys Gln Asn Cys Glu Leu Phe Glu Gln Leu Gly
                590                 595                 600

GAG TAC AAA TTC CAG AAT GCG CTA TTA GTT CGT TAC ACC AAG AAA GTA      1876
Glu Tyr Lys Phe Gln Asn Ala Leu Leu Val Arg Tyr Thr Lys Lys Val
                605                 610                 615

CCC CAA GTG TCA ACT CCA ACT CTT GTA GAG GTC TCA AGA AAC CTA GGA      1924
Pro Gln Val Ser Thr Pro Thr Leu Val Glu Val Ser Arg Asn Leu Gly
            620                 625                 630

AAA GTG GGC AGC AAA TGT TGT AAA CAT CCT GAA GCA AAA AGA ATG CCC      1972
Lys Val Gly Ser Lys Cys Cys Lys His Pro Glu Ala Lys Arg Met Pro
635                 640                 645

TGT GCA GAA GAC TAT CTA TCC GTG GTC CTG AAC CAG TTA TGT GTG TTG      2020
Cys Ala Glu Asp Tyr Leu Ser Val Val Leu Asn Gln Leu Cys Val Leu
650                 655                 660                 665

CAT GAG AAA ACG CCA GTA AGT GAC AGA GTC ACC AAA TGC TGC ACA GAA      2068
His Glu Lys Thr Pro Val Ser Asp Arg Val Thr Lys Cys Cys Thr Glu
                670                 675                 680

TCC TTG GTG AAC AGG CGA CCA TGC TTT TCA GCT CTG GAA GTC GAT GAA      2116
Ser Leu Val Asn Arg Arg Pro Cys Phe Ser Ala Leu Glu Val Asp Glu
            685                 690                 695

ACA TAC GTT CCC AAA GAG TTT AAT GCT GAA ACA TTC ACC TTC CAT GCA      2164
Thr Tyr Val Pro Lys Glu Phe Asn Ala Glu Thr Phe Thr Phe His Ala
        700                 705                 710

GAT ATA TGC ACA CTT TCT GAG AAG GAG AGA CAA ATC AAG AAA CAA ACT      2212
Asp Ile Cys Thr Leu Ser Glu Lys Glu Arg Gln Ile Lys Lys Gln Thr
715                 720                 725

GCA CTT GTT GAG CTT GTG AAA CAC AAG CCC AAG GCA ACA AAA GAG CAA      2260
Ala Leu Val Glu Leu Val Lys His Lys Pro Lys Ala Thr Lys Glu Gln
730                 735                 740                 745

CTG AAA GCT GTT ATG GAT GAT TTC GCA GCT TTT GTA GAG AAG TGC TGC      2308
Leu Lys Ala Val Met Asp Asp Phe Ala Ala Phe Val Glu Lys Cys Cys
                750                 755                 760

AAG GCT GAC GAT AAG GAG ACC TGC TTT GCC GAG GAG GGT AAA AAA CTT      2356
```

| Lys | Ala | Asp | Asp | Lys | Glu | Thr | Cys | Phe | Ala | Glu | Glu | Gly | Lys | Lys | Leu |
|---|---|---|---|---|---|---|---|---|---|---|---|---|---|---|---|
| | | | 765 | | | | 770 | | | | | | 775 | | |

| GTT | GCT | GCA | AGT | CAA | GCT | GCC | TTA | GGC | TTA | TAACATCACA | TTTAAAAGCA | | 2406 |
|---|---|---|---|---|---|---|---|---|---|---|---|---|---|
| Val | Ala | Ala | Ser | Gln | Ala | Ala | Leu | Gly | Leu | | | | |
| | | | 780 | | | | 785 | | | | | | |

TCTCAGCCTA CCATGAGAAT AAGAGAAAGA AAATGAAGAT CAAAAGCTT 2455

( 2 ) INFORMATION FOR SEQ ID NO:4:

( i ) SEQUENCE CHARACTERISTICS:
        ( A ) LENGTH: 787 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Lys | Trp | Val | Thr | Phe | Ile | Ser | Leu | Leu | Phe | Leu | Phe | Ser | Ser | Ala |
|---|---|---|---|---|---|---|---|---|---|---|---|---|---|---|---|
| 1 | | | | 5 | | | | | 10 | | | | | 15 | |

| Tyr | Ser | Arg | Gly | Val | Phe | Arg | Arg | Thr | Pro | Leu | Gly | Pro | Ala | Ser | Ser |
|---|---|---|---|---|---|---|---|---|---|---|---|---|---|---|---|
| | | | 20 | | | | | 25 | | | | | 30 | | |

| Leu | Pro | Gln | Ser | Phe | Leu | Leu | Lys | Cys | Leu | Glu | Gln | Val | Arg | Lys | Ile |
|---|---|---|---|---|---|---|---|---|---|---|---|---|---|---|---|
| | | | 35 | | | | 40 | | | | | 45 | | | |

| Gln | Gly | Asp | Gly | Ala | Ala | Leu | Gln | Glu | Lys | Leu | Cys | Ala | Thr | Tyr | Lys |
|---|---|---|---|---|---|---|---|---|---|---|---|---|---|---|---|
| | 50 | | | | | 55 | | | | | 60 | | | | |

| Leu | Cys | His | Pro | Glu | Glu | Leu | Val | Leu | Leu | Gly | His | Ser | Leu | Gly | Ile |
|---|---|---|---|---|---|---|---|---|---|---|---|---|---|---|---|
| 65 | | | | | 70 | | | | | 75 | | | | | 80 |

| Pro | Trp | Ala | Pro | Leu | Ser | Ser | Cys | Pro | Ser | Gln | Ala | Leu | Gln | Leu | Ala |
|---|---|---|---|---|---|---|---|---|---|---|---|---|---|---|---|
| | | | | 85 | | | | | 90 | | | | | 95 | |

| Gly | Cys | Leu | Ser | Gln | Leu | His | Ser | Gly | Leu | Phe | Leu | Tyr | Gln | Gly | Leu |
|---|---|---|---|---|---|---|---|---|---|---|---|---|---|---|---|
| | | | 100 | | | | | 105 | | | | | 110 | | |

| Leu | Gln | Ala | Leu | Glu | Gly | Ile | Ser | Pro | Glu | Leu | Gly | Pro | Thr | Leu | Asp |
|---|---|---|---|---|---|---|---|---|---|---|---|---|---|---|---|
| | | | 115 | | | | | 120 | | | | | 125 | | |

| Thr | Leu | Gln | Leu | Asp | Val | Ala | Asp | Phe | Ala | Thr | Thr | Ile | Trp | Gln | Gln |
|---|---|---|---|---|---|---|---|---|---|---|---|---|---|---|---|
| | 130 | | | | | 135 | | | | | 140 | | | | |

| Met | Glu | Glu | Leu | Gly | Met | Ala | Pro | Ala | Leu | Gln | Pro | Thr | Gln | Gly | Ala |
|---|---|---|---|---|---|---|---|---|---|---|---|---|---|---|---|
| 145 | | | | | 150 | | | | | 155 | | | | | 160 |

| Met | Pro | Ala | Phe | Ala | Ser | Ala | Phe | Gln | Arg | Arg | Ala | Gly | Gly | Val | Leu |
|---|---|---|---|---|---|---|---|---|---|---|---|---|---|---|---|
| | | | | 165 | | | | | 170 | | | | | 175 | |

| Val | Ala | Ser | His | Leu | Gln | Ser | Phe | Leu | Glu | Val | Ser | Tyr | Arg | Val | Leu |
|---|---|---|---|---|---|---|---|---|---|---|---|---|---|---|---|
| | | | 180 | | | | | 185 | | | | | 190 | | |

| Arg | His | Leu | Ala | Gln | Pro | Gly | Gly | Gly | Asp | Ala | His | Lys | Ser | Glu |
|---|---|---|---|---|---|---|---|---|---|---|---|---|---|---|
| | | 195 | | | | | 200 | | | | | 205 | | |

| Val | Ala | His | Arg | Phe | Lys | Asp | Leu | Gly | Glu | Glu | Asn | Phe | Lys | Ala | Leu |
|---|---|---|---|---|---|---|---|---|---|---|---|---|---|---|---|
| | 210 | | | | | 215 | | | | | 220 | | | | |

| Val | Leu | Ile | Ala | Phe | Ala | Gln | Tyr | Leu | Gln | Gln | Cys | Pro | Phe | Glu | Asp |
|---|---|---|---|---|---|---|---|---|---|---|---|---|---|---|---|
| 225 | | | | | 230 | | | | | 235 | | | | | 240 |

| His | Val | Lys | Leu | Val | Asn | Glu | Val | Thr | Glu | Phe | Ala | Lys | Thr | Cys | Val |
|---|---|---|---|---|---|---|---|---|---|---|---|---|---|---|---|
| | | | | 245 | | | | | 250 | | | | | 255 | |

| Ala | Asp | Glu | Ser | Ala | Glu | Asn | Cys | Asp | Lys | Ser | Leu | His | Thr | Leu | Phe |
|---|---|---|---|---|---|---|---|---|---|---|---|---|---|---|---|
| | | | 260 | | | | | 265 | | | | | 270 | | |

| Gly | Asp | Lys | Leu | Cys | Thr | Val | Ala | Thr | Leu | Arg | Glu | Thr | Tyr | Gly | Glu |
|---|---|---|---|---|---|---|---|---|---|---|---|---|---|---|---|
| | | 275 | | | | | 280 | | | | | 285 | | | |

| Met | Ala | Asp | Cys | Cys | Ala | Lys | Gln | Glu | Pro | Glu | Arg | Asn | Glu | Cys | Phe |
|---|---|---|---|---|---|---|---|---|---|---|---|---|---|---|---|
| | 290 | | | | | 295 | | | | | 300 | | | | |

| Leu | Gln | His | Lys | Asp | Asp | Asn | Pro | Asn | Leu | Pro | Arg | Leu | Val | Arg | Pro |
|---|---|---|---|---|---|---|---|---|---|---|---|---|---|---|---|
| 305 | | | | | 310 | | | | | 315 | | | | | 320 |

-continued

| | | | | | | | | | | | | | | |
|---|---|---|---|---|---|---|---|---|---|---|---|---|---|---|
| Glu | Val | Asp | Val | Met<br>325 | Cys | Thr | Ala | Phe | His<br>330 | Asp | Asn | Glu | Glu | Thr<br>335 | Phe |
| Leu | Lys | Lys | Tyr<br>340 | Leu | Tyr | Glu | Ile | Ala<br>345 | Arg | Arg | His | Pro<br>350 | Tyr | Phe | Tyr |
| Ala | Pro | Glu<br>355 | Leu | Leu | Phe | Phe | Ala<br>360 | Lys | Arg | Tyr | Lys | Ala<br>365 | Ala | Phe | Thr |
| Glu | Cys<br>370 | Cys | Gln | Ala | Ala | Asp<br>375 | Lys | Ala | Ala | Cys | Leu<br>380 | Leu | Pro | Lys | Leu |
| Asp<br>385 | Glu | Leu | Arg | Asp | Glu<br>390 | Gly | Lys | Ala | Ser | Ser<br>395 | Ala | Lys | Gln | Arg | Leu<br>400 |
| Lys | Cys | Ala | Ser | Leu<br>405 | Gln | Lys | Phe | Gly | Glu<br>410 | Arg | Ala | Phe | Lys | Ala<br>415 | Trp |
| Ala | Val | Ala | Arg<br>420 | Leu | Ser | Gln | Arg | Phe<br>425 | Pro | Lys | Ala | Glu | Phe<br>430 | Ala | Glu |
| Val | Ser | Lys<br>435 | Leu | Val | Thr | Asp | Leu<br>440 | Thr | Lys | Val | His | Thr<br>445 | Glu | Cys | Cys |
| His | Gly<br>450 | Asp | Leu | Leu | Glu | Cys<br>455 | Ala | Asp | Asp | Arg | Ala<br>460 | Asp | Leu | Ala | Lys |
| Tyr<br>465 | Ile | Cys | Glu | Asn | Gln<br>470 | Asp | Ser | Ile | Ser | Ser<br>475 | Lys | Leu | Lys | Glu | Cys<br>480 |
| Cys | Glu | Lys | Pro | Leu<br>485 | Leu | Glu | Lys | Ser | His<br>490 | Cys | Ile | Ala | Glu | Val<br>495 | Glu |
| Asn | Asp | Glu | Met<br>500 | Pro | Ala | Asp | Leu | Pro<br>505 | Ser | Leu | Ala | Ala | Asp<br>510 | Phe | Val |
| Glu | Ser | Lys<br>515 | Asp | Val | Cys | Lys | Asn<br>520 | Tyr | Ala | Glu | Ala | Lys<br>525 | Asp | Val | Phe |
| Leu | Gly | Met<br>530 | Phe | Leu | Tyr | Glu<br>535 | Tyr | Ala | Arg | Arg | His<br>540 | Pro | Asp | Tyr | Ser |
| Val<br>545 | Val | Leu | Leu | Leu | Arg<br>550 | Leu | Ala | Lys | Thr | Tyr<br>555 | Glu | Thr | Thr | Leu | Glu<br>560 |
| Lys | Cys | Cys | Ala | Ala<br>565 | Ala | Asp | Pro | His | Glu<br>570 | Cys | Tyr | Ala | Lys | Val<br>575 | Phe |
| Asp | Glu | Phe | Lys<br>580 | Pro | Leu | Val | Glu | Glu<br>585 | Pro | Gln | Asn | Leu | Ile<br>590 | Lys | Gln |
| Asn | Cys | Glu<br>595 | Leu | Phe | Glu | Gln | Leu<br>600 | Gly | Glu | Tyr | Lys | Phe<br>605 | Gln | Asn | Ala |
| Leu | Leu<br>610 | Val | Arg | Tyr | Thr | Lys<br>615 | Lys | Val | Pro | Gln | Val<br>620 | Ser | Thr | Pro | Thr |
| Leu<br>625 | Val | Glu | Val | Ser | Arg<br>630 | Asn | Leu | Gly | Lys | Val<br>635 | Gly | Ser | Lys | Cys | Cys<br>640 |
| Lys | His | Pro | Glu | Ala<br>645 | Lys | Arg | Met | Pro | Cys<br>650 | Ala | Glu | Asp | Tyr | Leu<br>655 | Ser |
| Val | Val | Leu | Asn<br>660 | Gln | Leu | Cys | Val | Leu<br>665 | His | Glu | Lys | Thr | Pro<br>670 | Val | Ser |
| Asp | Arg | Val<br>675 | Thr | Lys | Cys | Cys | Thr<br>680 | Glu | Ser | Leu | Val | Asn<br>685 | Arg | Arg | Pro |
| Cys | Phe<br>690 | Ser | Ala | Leu | Glu | Val<br>695 | Asp | Glu | Thr | Tyr | Val<br>700 | Pro | Lys | Glu | Phe |
| Asn<br>705 | Ala | Glu | Thr | Phe | Thr<br>710 | Phe | His | Ala | Asp | Ile<br>715 | Cys | Thr | Leu | Ser | Glu<br>720 |
| Lys | Glu | Arg | Gln | Ile<br>725 | Lys | Lys | Gln | Thr | Ala<br>730 | Leu | Val | Glu | Leu | Val<br>735 | Lys |
| His | Lys | Pro | Lys | Ala | Thr | Lys | Glu | Gln | Leu | Lys | Ala | Val | Met | Asp | Asp |

|     | 740 |     |     |     |     | 745 |     |     |     |     | 750 |     |     |
| --- | --- | --- | --- | --- | --- | --- | --- | --- | --- | --- | --- | --- | --- |
| Phe | Ala | Ala | Phe | Val | Glu | Lys | Cys | Cys | Lys | Ala | Asp | Asp | Lys | Glu | Thr |
|     |     | 755 |     |     |     |     | 760 |     |     |     |     | 765 |     |     |     |

| Cys | Phe | Ala | Glu | Glu | Gly | Lys | Lys | Leu | Val | Ala | Ala | Ser | Gln | Ala | Ala |
| --- | --- | --- | --- | --- | --- | --- | --- | --- | --- | --- | --- | --- | --- | --- | --- |
|     | 770 |     |     |     |     | 775 |     |     |     |     | 780 |     |     |     |     |

Leu Gly Leu
785

(2) INFORMATION FOR SEQ ID NO:5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

GGCCNNNNNG GCC                                       13

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

CAAGGATCCA AGCTTCAGGG CTGCGCAAGG TGGCGTAG             38

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

CGGGGTACCT TAGGCTTAAC CCCCTGGGC CCTGCCAGC             39

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

TTAGGCTTAG GTGGTGGCGG TACCCCCCTG GGCC                 34

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:9:

CAGGGGGGTA CCGCCACCAC CTAAGCC 27

(2) INFORMATION FOR SEQ ID NO:10:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:10:

GTTCTACGCC ACCTTGCGCA GCCCGGTGGA GGCGGTGATG CACACAAGAG TGAGGTTGCT 60

CATCGG 66

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:11:

CAGGGAGCTG GCAGGGCCCA GGGGGGTTCG ACGAAACACA CCCCTGGAAT AAGCCGAGCT 60

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: other nucleic acid (x i) SEQUENCE DESCRIPTION: SEQ ID NO:12:

GAAATGCATA AGCTCTTGCC ATTCTCACCG 30